US009572670B2

(12) United States Patent
Iannotti

(10) Patent No.: US 9,572,670 B2
(45) Date of Patent: Feb. 21, 2017

(54) PROSTHETIC ARTICULATION SURFACE MOUNTING

(71) Applicant: THE CLEVELAND CLINIC FOUNDATION, Cleveland, OH (US)

(72) Inventor: Joseph P. Iannotti, Strongsville, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/993,118

(22) Filed: Jan. 12, 2016

(65) Prior Publication Data

US 2016/0120650 A1   May 5, 2016

Related U.S. Application Data

(62) Division of application No. 14/206,701, filed on Mar. 12, 2014, now Pat. No. 9,241,804.

(60) Provisional application No. 61/787,216, filed on Mar. 15, 2013.

(51) Int. Cl.
| A61F 2/30 | (2006.01) |
| A61F 2/40 | (2006.01) |
| A61F 2/32 | (2006.01) |
| A61F 2/44 | (2006.01) |

(52) U.S. Cl.
CPC . *A61F 2/30* (2013.01); *A61F 2/32* (2013.01); *A61F 2/4081* (2013.01); *A61F 2/44* (2013.01); *A61F 2/30749* (2013.01); *A61F 2002/30332* (2013.01); *A61F 2002/30433* (2013.01); *A61F 2002/30507* (2013.01); *A61F 2002/30574* (2013.01); *A61F 2002/30604* (2013.01); *A61F 2002/30736* (2013.01); *A61F 2220/0008* (2013.01); *A61F 2220/0025* (2013.01); *A61F 2230/0063* (2013.01)

(58) Field of Classification Search
CPC ............... A61F 2/30; A61F 2/32; A61F 2/44; A61F 2/4081
See application file for complete search history.

*Primary Examiner* — Jason-Dennis Stewart
(74) *Attorney, Agent, or Firm* — Tarolli, Sundheim, Covell & Tummino LLP

(57) ABSTRACT

An apparatus for facilitating the mounting of a prosthetic articulation surface to a patient tissue includes an anchoring base including a central fastener aperture extending longitudinally therethrough. A first base end is laterally spaced from the central fastener aperture. A second base end is laterally spaced from the first base end with the central fastener aperture laterally interposed therebetween. Both of the first and second base ends include a plate engagement feature. An anchor plate includes a central coupler aperture extending longitudinally therethrough. An outer perimeter is spaced laterally apart from the central coupler aperture. A plate rim extends laterally inward from the outer perimeter to substantially laterally surround the central coupler aperture. At least one plate fastener aperture extends longitudinally through the plate rim. At least one base engagement feature is located on the plate rim and is selectively engageable with the plate engagement feature of the anchoring base.

10 Claims, 29 Drawing Sheets

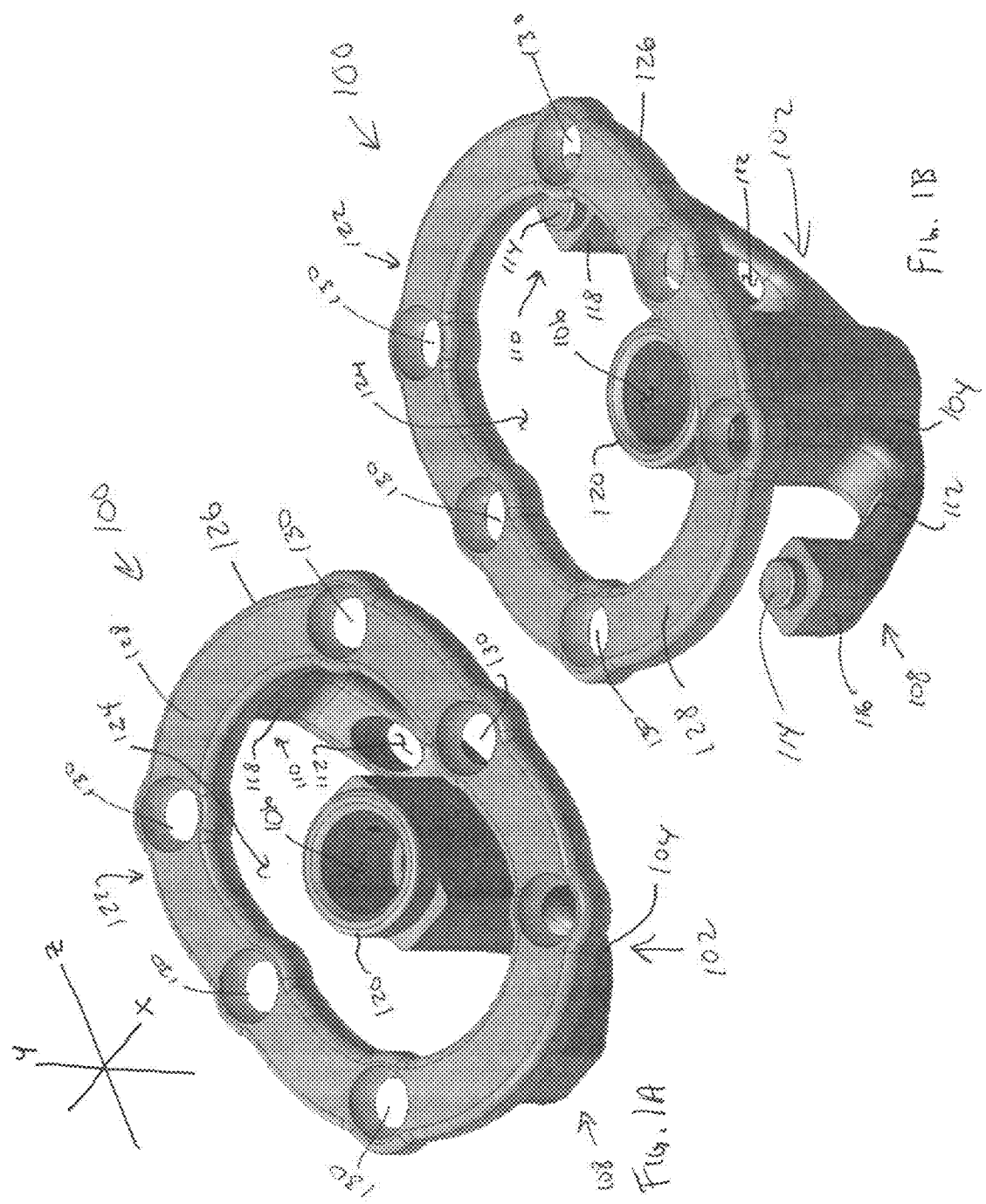

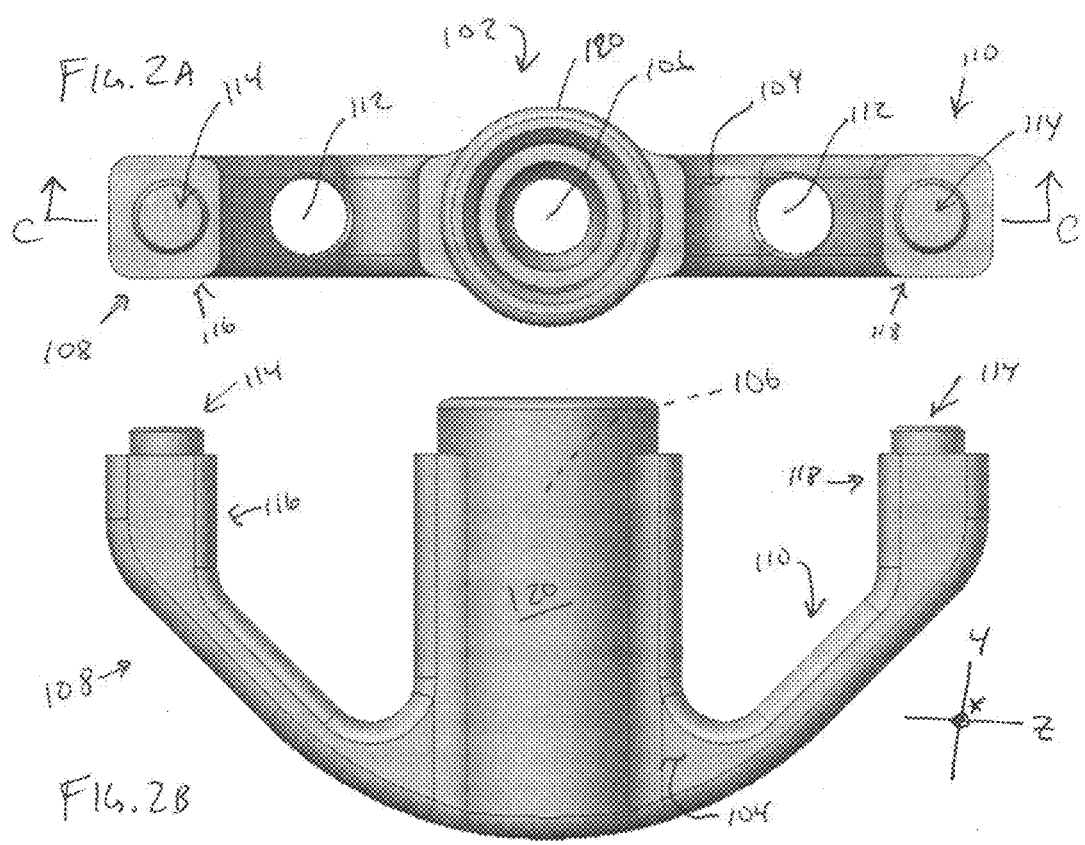

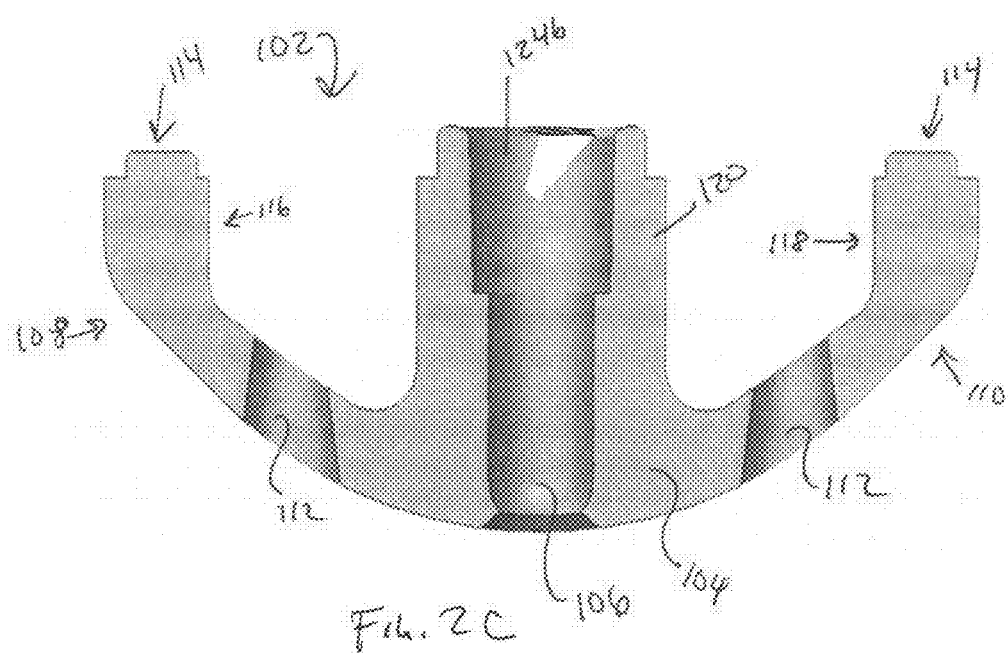

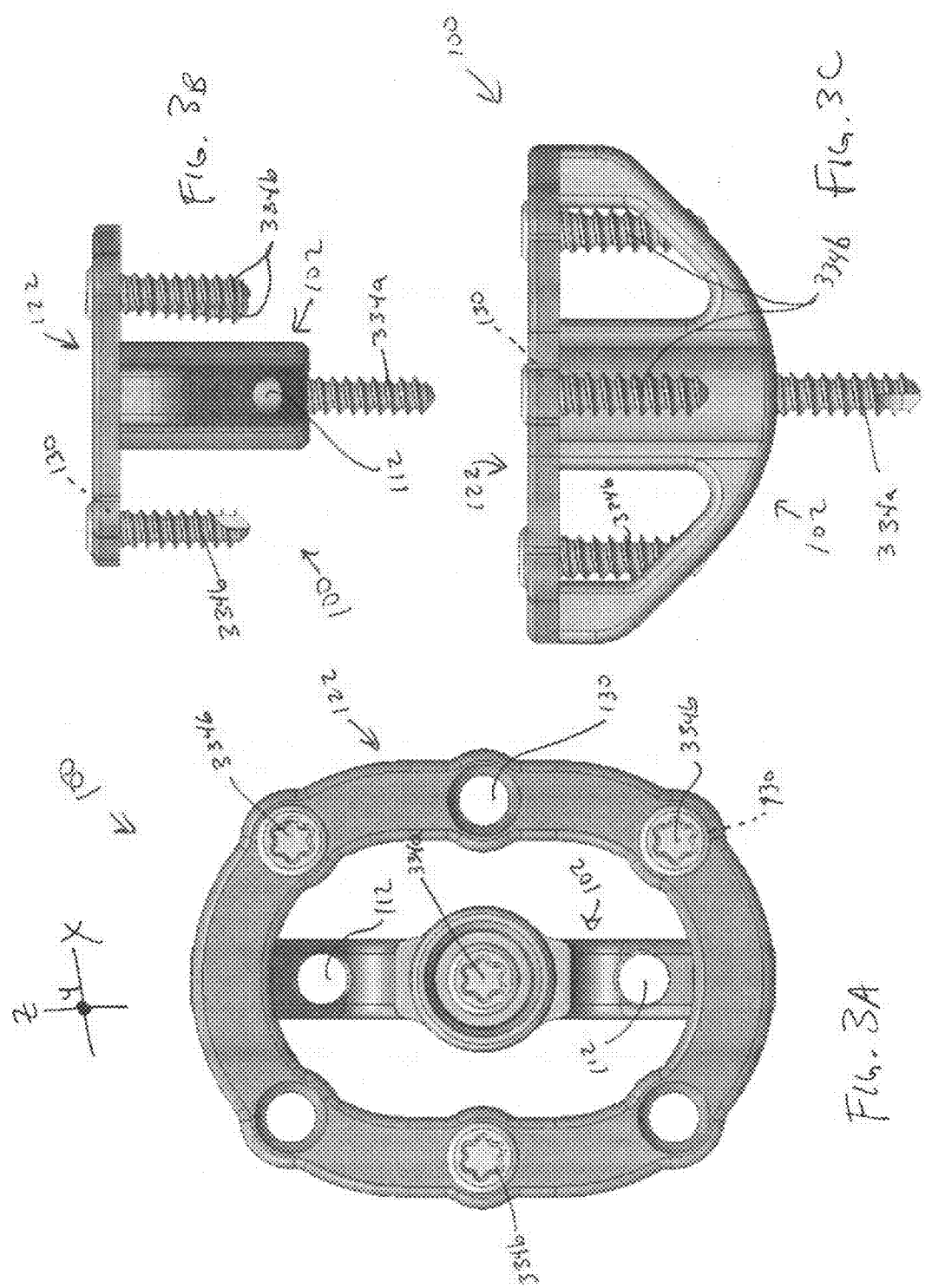

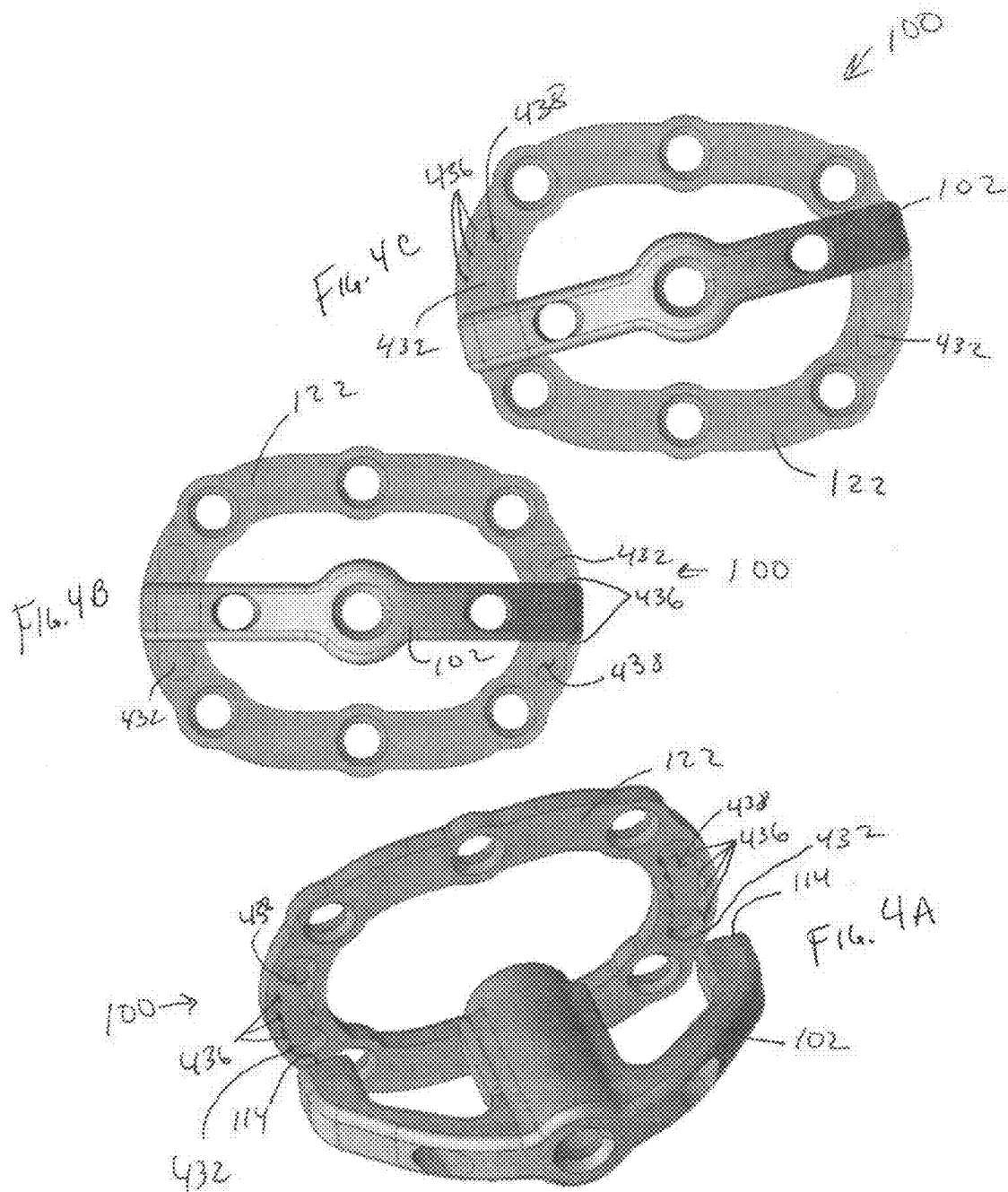

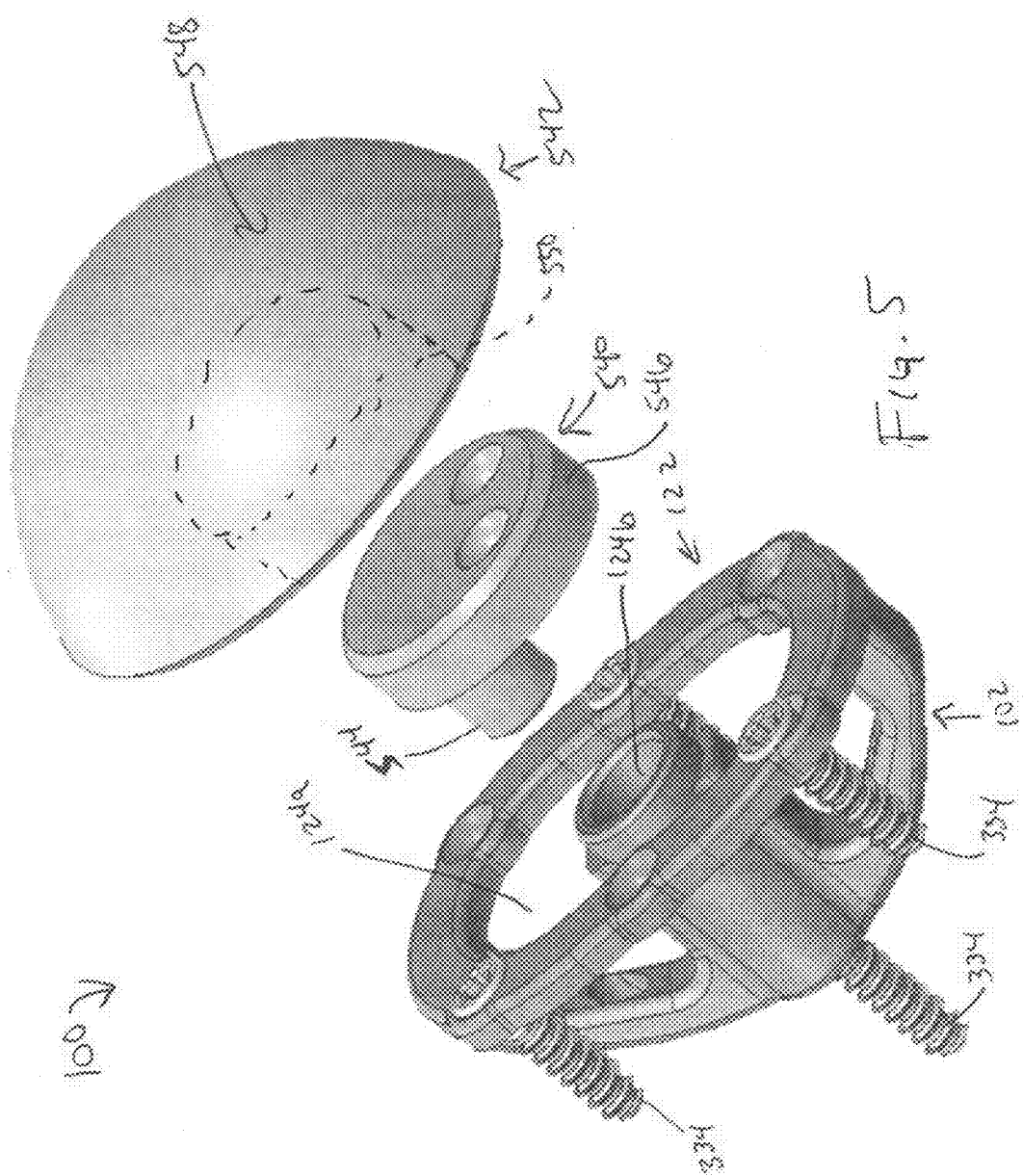

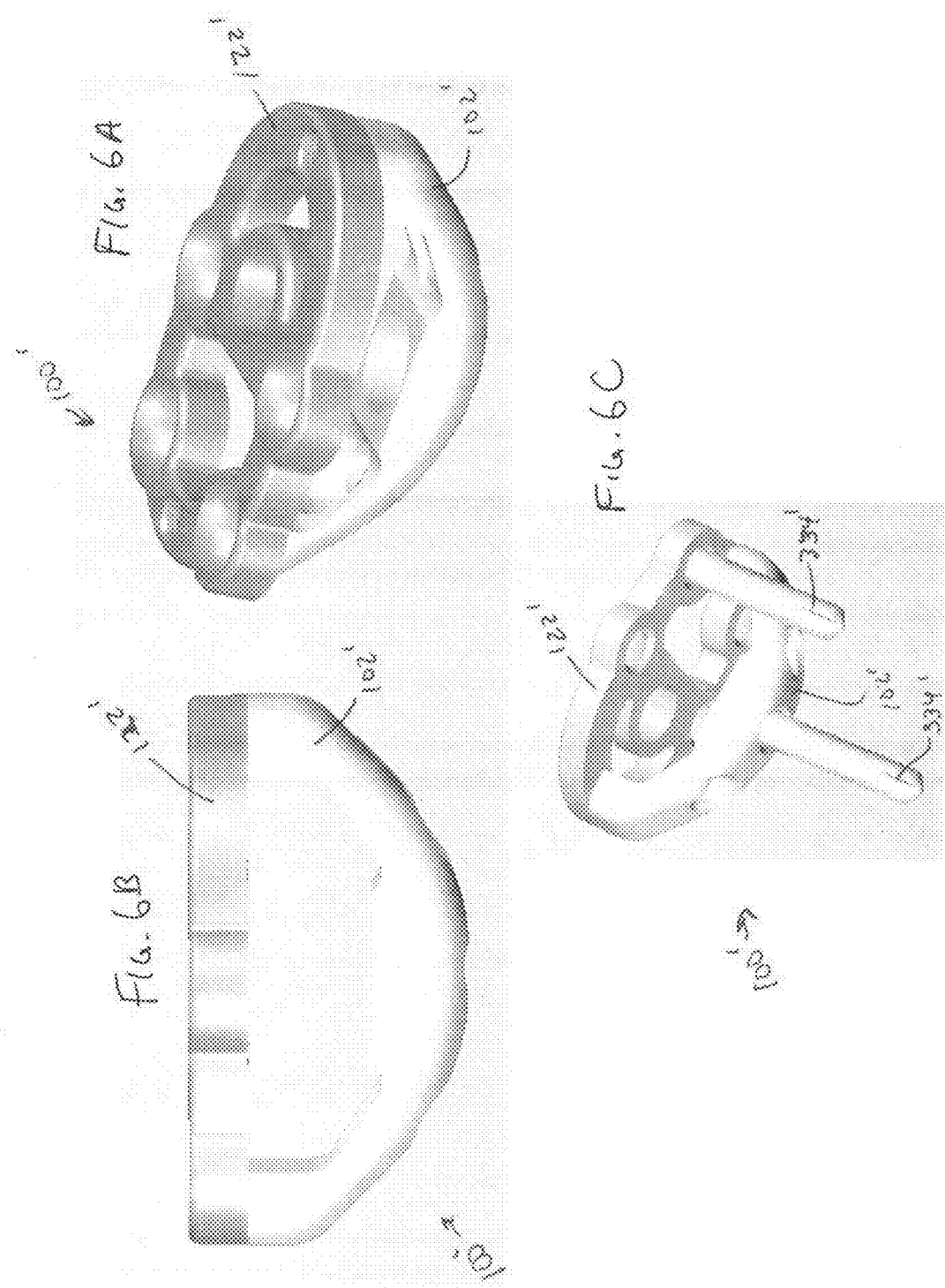

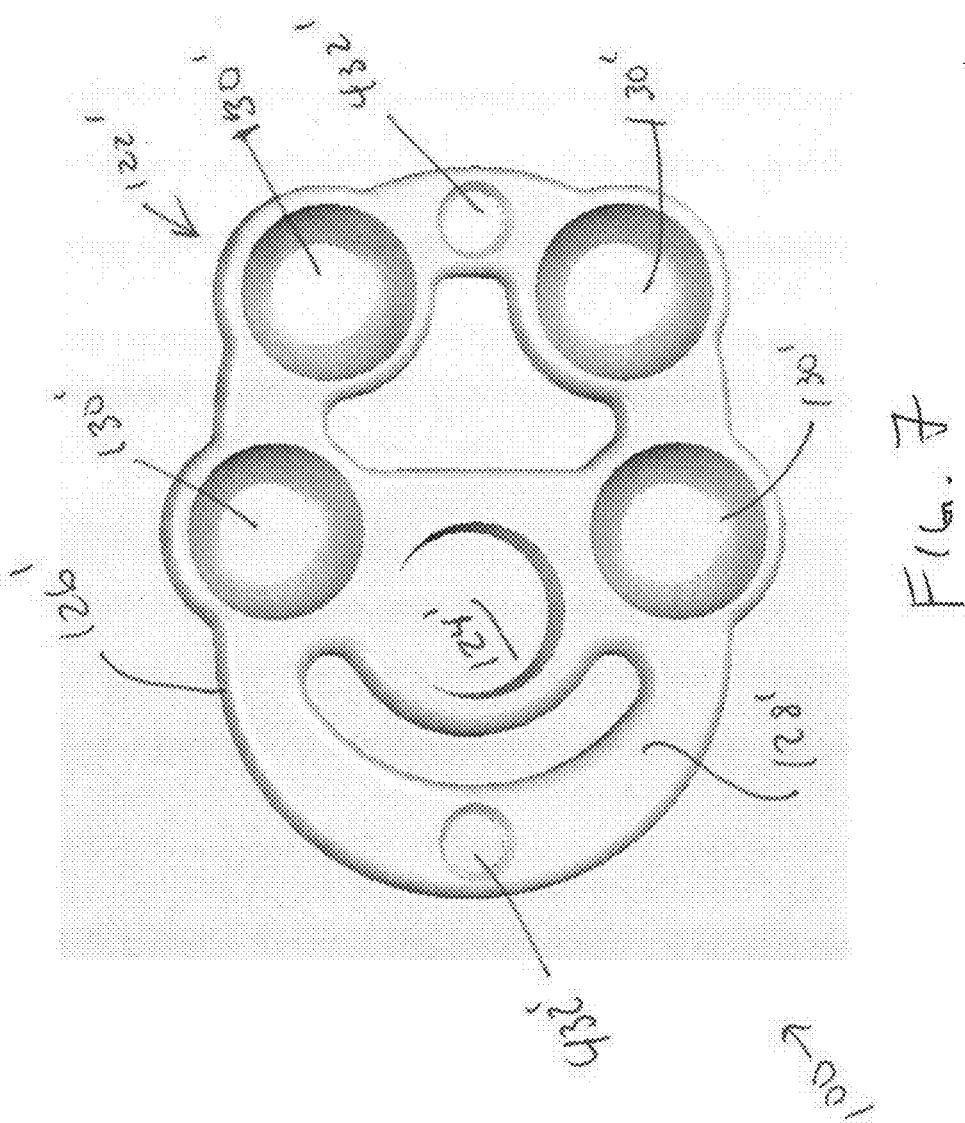

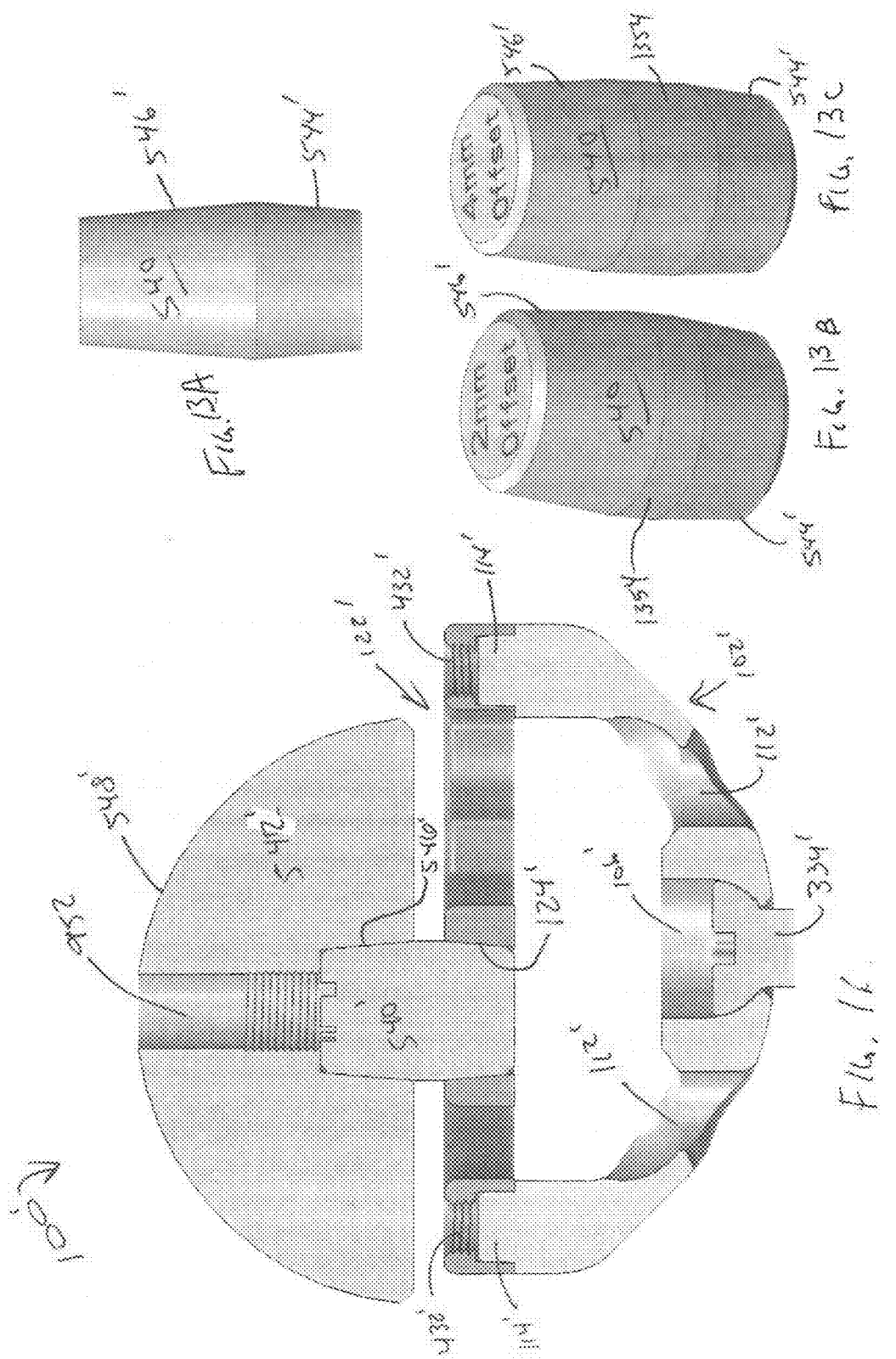

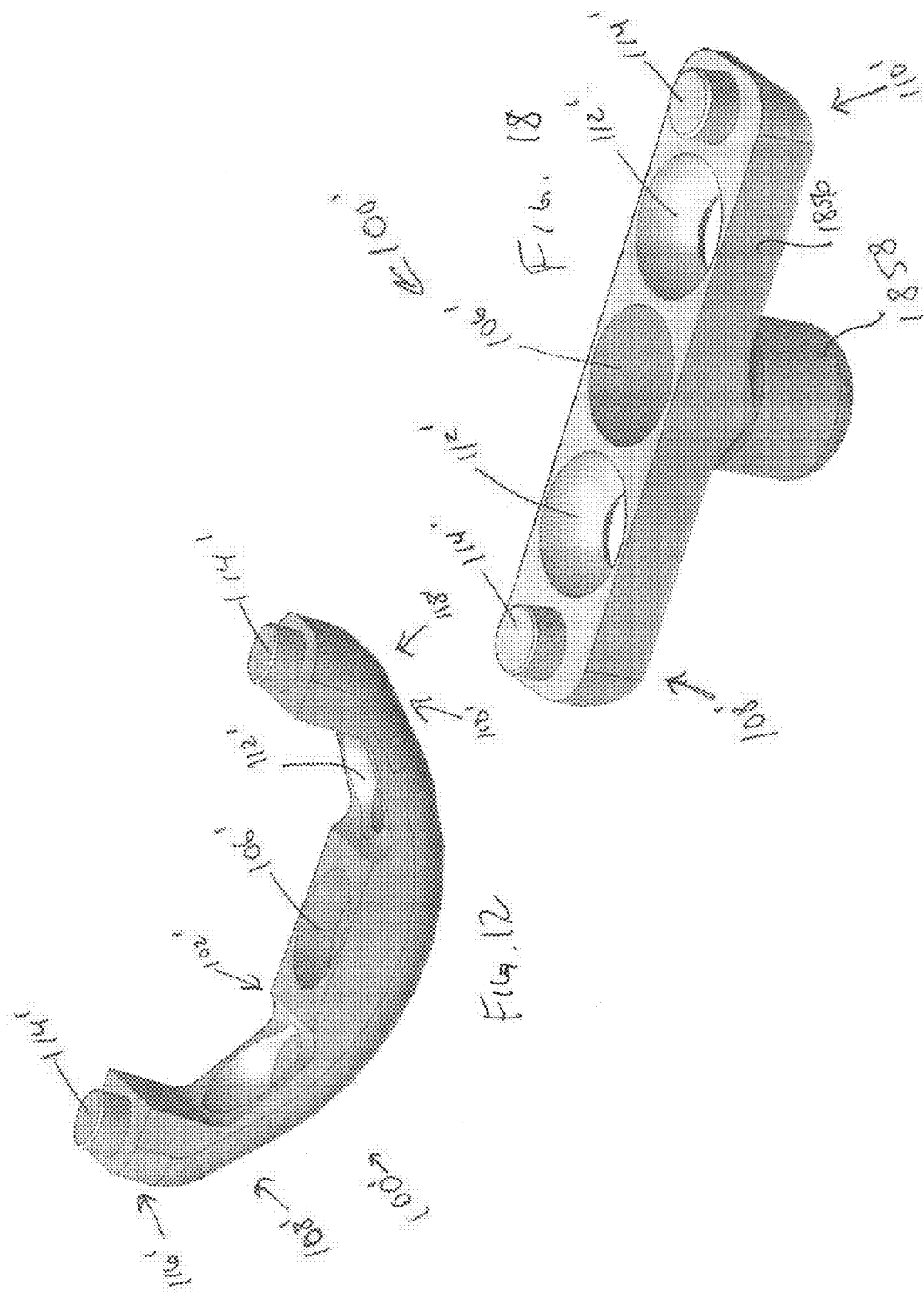

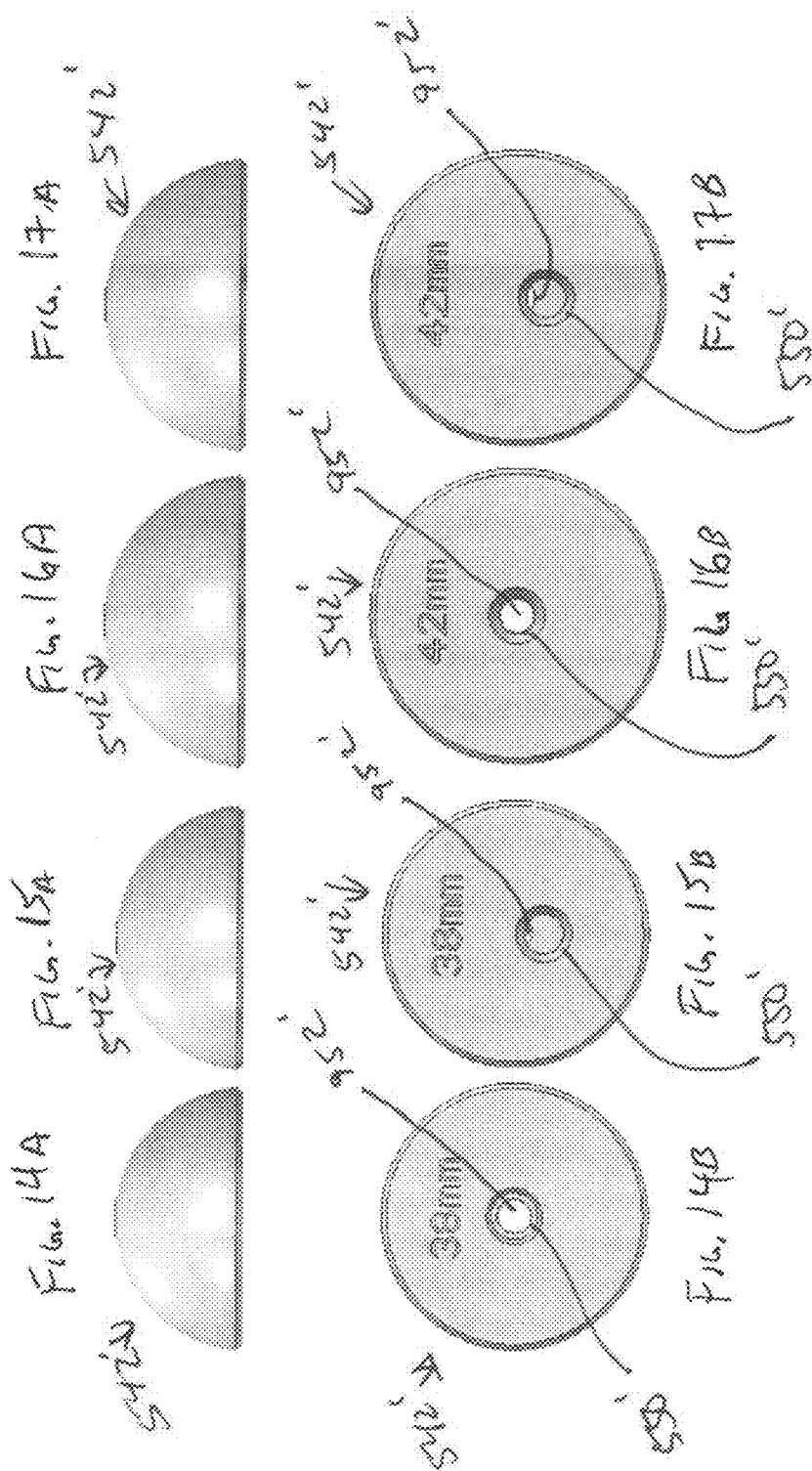

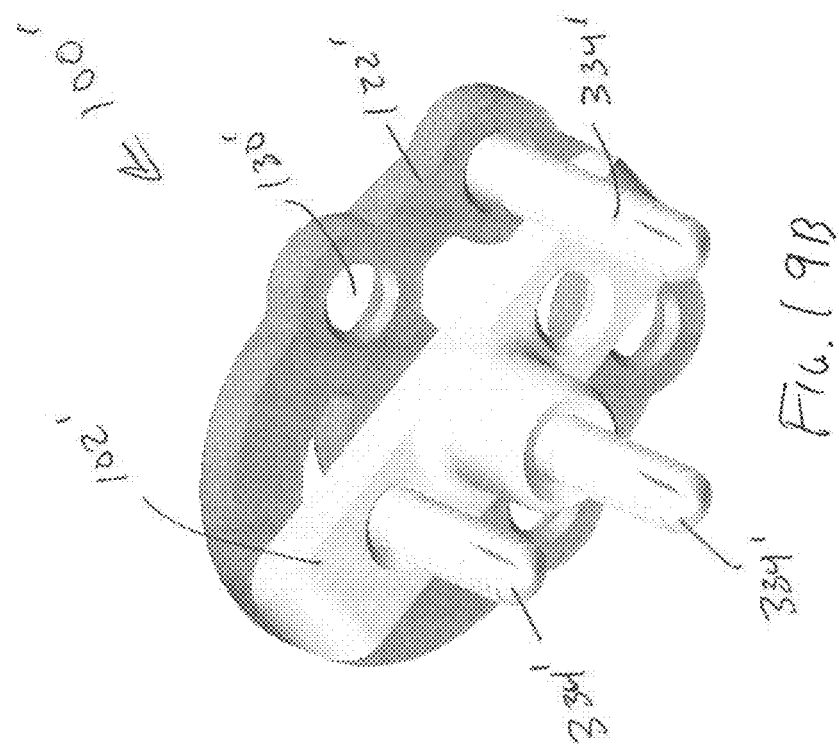
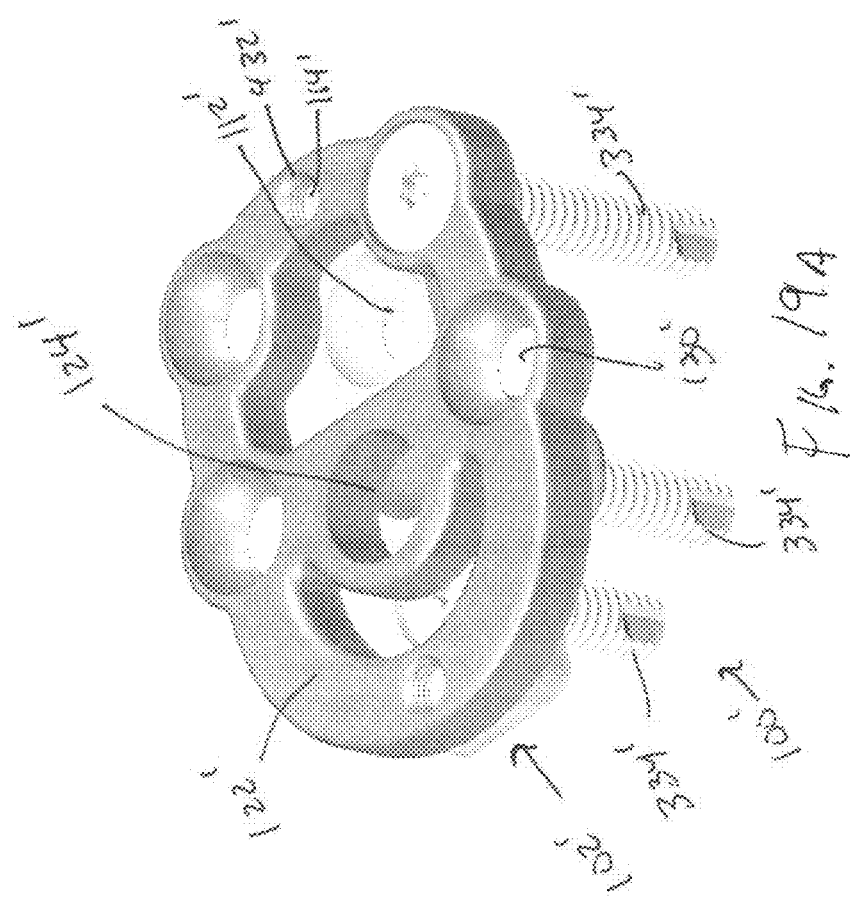

PROSTHETIC ARTICULATION SURFACE MOUNTING

RELATED APPLICATION

This application is a divisional of U.S. patent application Ser. No. 14/206,701, filed 12 Mar. 2014, which claims priority from U.S. Provisional Application No. 61/787,216, filed 15 Mar. 2013, the subject matter of both of which is incorporated herein by reference in its entirety.

TECHNICAL FIELD

The present invention relates to an apparatus and method for use of a prosthetic articulation surface mounting and, more particularly, to a method and apparatus for facilitating the mounting of a prosthetic articulation surface to a patient tissue.

BACKGROUND OF THE INVENTION

In the installation of a prosthetic shoulder joint into a patient's body, a glenoid component is implanted into the glenoid vault of the patient's scapula. An obverse surface of the glenoid component is configured for articulating contact with a humeral component carried by the patient's humerus. A reverse surface of the glenoid component is secured to the bone surface of the glenoid vault. A shoulder arthroplasty can be either "primary" (where the humeral component is the "ball" and the glenoid component is the "socket" in the articulating relationship) or "reverse" (where the glenoid component is the "ball" and the humeral component is the "socket" in the articulating relationship).

Because a shoulder prosthesis is normally provided to correct a congenital or acquired defect of the native shoulder joint, the glenoid vault often exhibits a pathologic, nonstandard anatomic configuration, such as by exhibiting cavitary bone loss. One attribute of shoulder repair surgery is the rather limited volume of anatomical, "healthy" bone in the glenoid to provide sturdy anchorage for the glenoid component. This problem may be exacerbated in a revision surgery, where removing the original prosthetic component may result in additional damage to, or loss of, the underlying bone.

SUMMARY OF THE INVENTION

In an embodiment of the present invention, an apparatus for facilitating the mounting of a prosthetic articulation surface to a patient tissue is described. An anchoring base includes a central fastener aperture extending longitudinally therethrough. A first base end is laterally spaced from the central fastener aperture. A second base end is laterally spaced from the first base end with the central fastener aperture laterally interposed therebetween. Both of the first and second base ends include a plate engagement feature. An anchor plate includes a central coupler aperture extending longitudinally therethrough. An outer perimeter is spaced laterally apart from the central coupler aperture. A plate rim extends laterally inward from the outer perimeter to substantially laterally surround the central coupler aperture. At least one plate fastener aperture extends longitudinally through the plate rim. At least one base engagement feature is located on the plate rim and is selectively engageable with the plate engagement feature of the anchoring base.

In an embodiment of the present invention, a method of facilitating the mounting of a prosthetic articulation surface to a patient tissue is described. An apparatus is provided. The apparatus includes an anchoring base including a central fastener aperture extending longitudinally therethrough. A first base end is laterally spaced from the central fastener aperture. A second base end is laterally spaced from the first base end with the central fastener aperture laterally interposed therebetween. Both of the first and second base ends include a plate engagement feature. An anchor plate includes a central coupler aperture extending longitudinally therethrough. An outer perimeter is spaced laterally apart from the central coupler aperture. A plate rim extends laterally inward from the outer perimeter to substantially laterally surround the central coupler aperture. At least one plate fastener aperture extends longitudinally through the plate rim. At least one base engagement feature is located on the plate rim. At least a portion of the anchoring base is placed into a predetermined orientation with the patient tissue. A fastener is extended longitudinally through the central fastener aperture to secure the anchoring base to an underlying patient tissue surface. The anchor plate is placed longitudinally adjacent to the anchoring base. At least one base engagement feature of the anchor plate is engaged with a corresponding at least one plate engagement feature of the anchoring base.

BRIEF DESCRIPTION OF THE DRAWINGS

For a better understanding of the invention, reference may be made to the accompanying drawings, in which:

FIG. 1A is a partial perspective view of an embodiment of the present invention;

FIG. 1B is a partial exploded view of the embodiment of FIG. 1A;

FIG. 2A is a top view of a component of the embodiment of FIG. 1A;

FIG. 2B is a side view of the component of FIG. 2A;

FIG. 2C is a cross-sectional view taken along line C-C of FIG. 2A;

FIG. 3A is a partial top view of the embodiment of FIG. 1A;

FIG. 3B is a partial front view of the embodiment of FIG. 1A;

FIG. 3C is a partial side view of the embodiment of FIG. 1A;

FIG. 4A is a partial exploded perspective view of the embodiment of FIG. 1A;

FIG. 4B is a partial bottom view of the embodiment of FIG. 1A in a first configuration;

FIG. 4C is a partial bottom view of the embodiment of FIG. 1A in a second configuration;

FIG. 5 is a partially exploded perspective view of the embodiment of FIG. 1A;

FIG. 6A is a partial top perspective view of an embodiment of the present invention;

FIG. 6B is a partial front view of the embodiment of FIG. 6A;

FIG. 6C is a partial bottom perspective view of the embodiment of FIG. 6A;

FIG. 7 is a top view of a component of the embodiment of FIG. 6A;

FIG. 11 is a cross-sectional view taken along line 11-11 of FIG. 9;

FIG. 12 is a perspective view of a component of the embodiment of FIG. 6A in a first configuration;

FIG. 13A is a side view of a component of any embodiment of the present invention in a first configuration;

FIG. 13B is a side view of the component of FIG. 16A in a second configuration;

FIG. 13C is a side view of the component of FIG. 16A in a third configuration;

FIGS. 14A and 14B are side and bottom views, respectively, of a component of any embodiment of the present invention in a first configuration;

FIGS. 15A and 15B are side and bottom views, respectively, of the component of FIGS. 14A-14B in a second configuration;

FIGS. 16A and 16B are side and bottom views, respectively, of the component of FIGS. 14A-14B in a third configuration;

FIGS. 17A and 17B are side and bottom views, respectively, of the component of FIGS. 14A-14B in a fourth configuration;

FIG. 18 is a perspective view of a component of the embodiment of FIG. 6A in a second configuration;

FIG. 19A is a partial bottom perspective view of the embodiment of FIG. 18;

FIG. 19B is a partial bottom perspective view of the embodiment of FIG. 18;

FIGS. 26A-26H schematically depict an example use sequence of any embodiment of the present invention.

DESCRIPTION OF EMBODIMENTS

Figure 9:
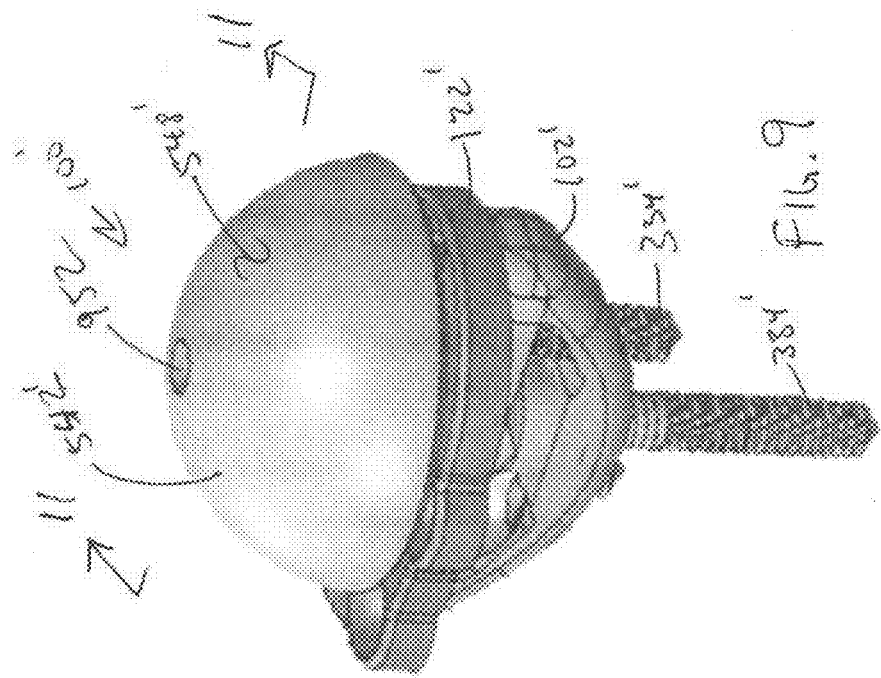
FIG. 9 is a partial perspective view of the embodiment of FIG. 6A.

Devices and methods of the present disclosure may be applied to any patient tissue surface, such as a cancellous bone surface, for any type of surgery, including, but not limited to, an implant for joint reconstruction, joint replacement, fracture fixation, or any other joint or spinal procedure. For example, embodiments may be used for the glenoid component for a shoulder arthroplasty that may obtain fixation from the metaphyseal and/or diaphyseal bone. The final placement/installation of the apparatus described and shown herein may facilitate the mounting of any articulating device for shoulder replacement. Embodiments may include placement of a spherical or semi-elliptical head for reverse shoulder arthroplasty or a socket-side component for primary shoulder arthroplasty. Embodiments may be applied to any bone surface, including, but not limited to, the distal femur or proximal tibia for total knee arthroplasty, the distal tibia or talus for ankle arthroplasty, the distal radius for fracture fixation or wrist arthroplasty, or the acetabulum or proximal femur for hip arthroplasty.

Embodiments may be configured for augmentation of a portion or all of the patient's bone. The apparatus described herein may be designed and placed to minimize disruption of the bone in areas around the implant and/or minimize disruption of the bone in areas spaced apart from the main functional portion of the implant. Use of bioactive materials may enhance bone structure (which may include bone matrix), allow for enhanced implant fixation, and/or be incorporated into the bone.

The methods and devices disclosed in the present disclosure may be used in conjunction with any medical procedure on the body, for example, during intervertebral disc surgery, kyphoplasty, knee surgery, hip surgery, organ transplant surgery, bariatric surgery, spinal surgery, anterior cruciate ligament ("ACL") surgery, posterior cruciate ligament ("PCL") surgery, tendon-ligament surgery, rotator cuff surgery, capsule repair surgery, fractured bone surgery, pelvic fracture surgery, avulsion fragment surgery, shoulder surgery, hernia repair surgery, and/or surgery for an intrasubstance ligament tear, annulus fibrosis, fascia lata, flexor tendons, or any other type of medical procedure.

As additional examples, applications for embodiments may include any type of prosthetic replacement devices that are implemented into possibly weak and/or cancellous bone. For example, this may include hip, knee, and shoulder replacements, internal fixation devices for fractures or fracture sequelae, suture anchors for soft tissue to bone repair, and external fixation devices. As a further example, embodiments may be used for orthopedic surgery, maxillofacial surgery, dental implants, or any other patient tissue operation.

The patient tissue is shown and described herein at least as a glenoid/scapula and the prosthetic implant component is shown and described herein at least as a prosthetic shoulder component, both to aid in depiction/description, but one of ordinary skill in the art will be able to use (optionally modified as appropriate) the described concepts and structures as desired for any patient use environment.

In the attached Figures, multiple instances of similar structures in the same Figure, or in different Figures, have not all been labeled with element numbers, to avoid undue visual clutter and resulting confusion. One of ordinary skill in the art will understand that, in a Figure having at least one structure called out with an element number, similar structures (whether in that Figure or in another Figure) can be considered to have the same element number.

Spatially relative terms, such as "under," "below," "lower," "over," "upper" and the like, may be used herein for ease of description to describe one element or feature's relationship to another element(s) or feature(s), as illustrated in the Figures. It will be understood that the spatially relative terms can encompass different orientations of a device in use or operation, in addition to the orientation(s) depicted in the Figures.

Since directions and orientations are used throughout this description, a three-dimensional coordinate system has been placed in FIG. 1A to clarify the references made herein. The "longitudinal" direction, as referenced herein, substantially corresponds to the Y-axis shown. A direction "lateral" to the Y-axis will lie substantially in a plane defined by the X- and Z-axes.

In accordance with the present invention, FIG. 1 depicts a partial view of an apparatus 100 for facilitating the mounting of a prosthetic articulation surface to a patient tissue (described herein, for example, as the mounting of a glenosphere prosthetic component to a glenoid). The apparatus 100 includes an anchoring base 102 having an anchoring base body 104. The anchoring base body 104 may be substantially planar with respect to the Y-Z plane, as shown in the Figures. The term "planar" is used herein to indicate that the "planar" structure is configured in a substantially "flat" manner. A "planar" structure is not required to be strictly two-dimensional and can include a thickness, optionally a slightly varying thickness, perpendicular to the plane. However, one of ordinary skill in the art will recognize that a structure having significant protrusions/extensions out of the defining plane, particularly those that are asymmetrical with respect to that plane, will fall outside the scope of "planar", as used herein. For example, the anchoring base body 104, as shown in the Figures, is considered to be planar with respect to the Y-Z plane, but can be seen to be not planar with respect to the X-Z plane.

The anchoring base 102 includes a central fastener aperture 106 extending longitudinally (i.e., parallel to the Y-axis) therethrough. A first base end 108 of the anchoring base 102 is laterally (i.e., along the X-Z plane) spaced from the central fastener aperture 106. A second base end 110 of the anchoring base 102 is laterally spaced from the first base end 108 with the central fastener aperture 106 laterally interposed therebetween. For example, and as shown in the Figures, the first base end 108, central fastener aperture 106, and second base end 110 may be spaced laterally apart substantially along a line parallel to the Z-axis.

At least one supplemental fastener aperture 112 may also be provided. When present, the supplemental fastener aperture(s) 112 may extend longitudinally through the anchoring base 102 and may each be laterally interposed between the central fastener aperture 106 and a chosen one of the first and second base ends 108 and 110.

Both of the first and second base ends 108 and 110 may include a plate engagement feature 114. As shown in the Figures, the plate engagement features 114 may be male stud-type protrusions from the first and second base ends 108 and 110. However, it is also contemplated that the plate engagement features 114 may be a female slot-type recess, an interlocking clip-type mechanism, or have any other structure desired to provide and/or assist with the functions described herein.

The plate engagement features 114 may be at least partially positioned on a topmost (in the orientation of FIG. 1A) surface of the first and second base ends 108 and 110, as shown. Also as shown, the first and/or second base ends 108 and 110 may include first and second arms 116 and 118 projecting longitudinally upward from a remaining portion of the anchoring base 102 spaced laterally from the central fastener aperture 106.

At least a portion of the central fastener aperture 106 may extend longitudinally through a fastener boss 120 projecting longitudinally upward from a remaining portion of the anchoring base 102 spaced laterally from the first and second base ends 108 and 110. The fastener boss 120 and first and second arms 116 and 118, when present, may project substantially longitudinally parallel to each other and may be substantially laterally spaced from each other, which may collectively provide a "trident" appearance or configuration to the anchoring base 102, as shown in FIGS. 1A-1B and FIGS. 2A-2C.

FIGS. 2A-2C depict the anchoring base 102 separately from other structures of the apparatus 100. As can be seen in FIG. 2A, the planar nature of the anchoring base 102 is apparent (the slight bulge of the anchoring base body 104 around the central fastener aperture 106 is not substantially out-of-plane to destroy the planarity). Particularly in the cross-sectional view of FIG. 2C, the "stepped" or variable-diameter nature of the central fastener aperture 106 is apparent and will be discussed in more detail below.

With reference back to FIGS. 1A-1B, the apparatus 100 may also include an anchor plate 122 including a central coupler aperture 124 extending longitudinally therethrough. The anchor plate 122 may be substantially planar, such as with respect to the X-Z plane as shown in the Figures. An outer perimeter 126 of the anchor plate 122 is spaced laterally apart from the central couple aperture 124. The outer perimeter 126, as the term is used herein, refers to the outside edge of an area or surface (i.e., the area defining the anchor plate 122). The outer perimeter 126 of the anchor plate 122 shown in FIGS. 1A-1B is a substantially ovoid "footprint" or silhouette that traces the outermost shape and area (e.g., of a surface onto which the anchor plate is projected) which is covered by the anchor plate.

A plate rim 128 extends laterally inward from the outer perimeter 126 to substantially laterally surround the central coupler aperture 124. In the embodiment shown in FIGS. 1A-1B, and due to the relatively large central coupler aperture 124 in this embodiment, the plate rim 128 substantially defines the entire material volume of the anchor plate 122. However, other configurations of a plate rim 128, where additional structures (e.g., crossbars) cooperate therewith to form the anchor plate 122, are contemplated, as will be discussed below.

At least one plate fastener aperture 130 may extend longitudinally through the plate rim 128. As with any apertures of the described embodiments, the plate rim 128 may be laterally thickened (e.g., the outer perimeter 126 may "bulge" laterally outward) to accommodate passage of another structure (e.g., a fastener) through the respective aperture, as described below, while providing desired mechanical properties to the structure through which the aperture extends.

At least one base engagement feature (shown at 432 in FIGS. 4A-4C and described in more detail below, with reference to those Figures) may be located on the plate rim 128 and may be selectively engageable with a respective plate engagement feature 114 of the anchoring base 102. The base engagement feature(s) 432 and/or corresponding plate engagement feature(s) 114 may be located on the respective anchor plate 122 and anchoring base 102 for substantially longitudinally-oriented engagement with each other. The term "longitudinally-oriented engagement" is used herein to indicate that relative longitudinal motion is primarily used to engage or disengage the base and plate engagement feature(s) 432 and 114 (e.g., motion such as that shown in the sequence of arrangement between FIGS. 1A and 1B), although it is also contemplated that some laterally-oriented motion may be secondarily used to fine-tune and/or secure the anchor plate 122 and anchoring base 102 into a desired configuration.

Turning now to FIGS. 3A-3C, a plurality of fasteners 334 are shown operatively engaged with respective apertures. For example, a fastener 334a is shown longitudinally extending through the central fastener aperture 106 to selectively secure the anchoring base 102 to an underlying patient tissue surface (omitted from FIGS. 3A-3C for clarity), as will be discussed below. Similarly, fasteners 334*b* are shown longitudinally extending through selected ones of the plate fastener apertures 130 to selectively secure the anchor plate 122 to an underlying patient tissue surface. Threaded one-piece fasteners 334 are shown in the Figures, but any style of rigid and/or flexible fasteners including, but not limited to, rivets, adhesives, bolts, nails, pins, clips, ties, or the like may be used, singly or in combination, for a particular use environment of the present invention.

It should be noted that one or more of the total available plate fastener apertures 130 of a particular anchor plate 122 can be used to accept fasteners 334*b* for a particular use environment of the present invention (optionally leaving other apertures of the apparatus 100 vacant, as shown in the Figures), and one of ordinary skill in the art will be able to select, provide, and locate any number of appropriately sized and configured fasteners 334 for any corresponding aperture of the apparatus 100 as desired. For example, and as shown in FIGS. 3A-3C, the supplemental fastener apertures 112 are left vacant, with no corresponding fasteners 334 associated therewith in these Figures. However, it is contemplated that one or more fasteners (not shown) may be substantially longitudinally extended through selected ones of the supplemental fastener apertures 112 to selectively secure the anchor plate 122 to an underlying patient tissue surface As previously mentioned, FIGS. 4A-4C depict details of the base engagement feature(s) 432 and/or corresponding plate engagement feature(s) 114, as located on the respective anchor plate 122 and anchoring base 102 for substantially longitudinally-oriented engagement with each other. In the exploded view of FIG. 4A, the base engagement features 432 of the anchor plate 122 can be seen to be female slot-type recesses on an underside of the plate rim 128. However, it is also contemplated that the base engagement features 432 may be a male stud-type protrusion or an interlocking clip-type mechanism, may be located on any other surface of the plate rim 128, and/or may have any other structure, positioning, or configuration desired to provide and/or assist with the functions described herein.

With reference to the exploded view of FIG. 4A and the assembled view of FIG. 4B, the anchor plate 122 and anchoring base 102 can be brought together substantially longitudinally to place the stud-type plate engagement features 114 of the anchoring base 102 into the slot-type base engagement features 432 of the anchor plate 122. The dimensions of the base engagement feature(s) 432 and/or corresponding plate engagement feature(s) 114 may be chosen to provide a press-fit (frictional-fit) therebetween which assists with holding the anchor plate 122 and anchoring base 102 together. Alternatively, some "play" or "slack" could be permitted between the base engagement feature(s) 432 and corresponding plate engagement feature(s) 114 such that engagement of these features helps with relatively locating the anchor plate 122 and anchoring base 102 with respect to one another without positive, operative coupling of these two structures.

As shown in the Figures, the base engagement features 432 may include a plurality of engagement stations 436, shown here as overlapping-diameter portions of a lobed slot 438, wherein the maximum diameter/width of each engagement station is configured to accept the plate engagement feature 114 while the minimum width is configured to prevent lateral sliding movement of the plate engagement feature with respect to the lobed slot. When present, the plurality of engagement stations 436 can facilitate selective engagement of the anchor plate 122 and anchoring base 102 in a selected one of a plurality of relative rotational orientations within a lateral plane, responsive to a selection of engagement station used for the engagement. For example, the plurality of rotational orientations of one of the anchor plate 122 and anchoring base 102 relative to the other may each correspond to a selected engagement station 436.

Stated differently, in FIG. 4B, the anchor plate 122 and anchoring base 102 are engaged together with the assistance of the plate engagement features 114 and base engagement features 432. Because the plate engagement features 114 are in a central one of the engagement stations 436 of the base engagement feature 432, the anchoring base 102 is aligned in a first configuration or a "base" position of 0° rotation with respect to the anchor plate 122—an example of a first rotational orientation.

Turning then to FIG. 4C, the anchoring base 102 and anchor plate 122 have been relatively rotated in a lateral plane such that the plate engagement features 114 are in endmost ones of the engagement stations 436 of the base engagement feature 432. Thus, in FIG. 4C, the anchoring base 102 is aligned in a second configuration or a "rotated" position of approximately 10° rotation from the first configuration with respect to the anchor plate 122.

Depending on the configuration of the plate engagement features 114, base engagement features 432, and/or engagement stations 436, the anchoring base 102 and anchor plate 122 may be substantially longitudinally separated from each other for movement between rotational orientations and then longitudinally re-engaged once the desired rotational orientation is reached. Alternately, the anchoring base 102 and anchor plate 122 may remain in their "engaged" longitudinal positions during relative rotation when the plate engagement features 114 and/or base engagement features 432 are designed to permit lateral rotation during longitudinal engagement. For example, the slot of the base engagement feature 432 could have a smooth-sided, not lobed, channel-type footprint to allow sliding of the stud-type plate engagement feature 114 with respect to the slot during full longitudinal engagement of the anchoring base 102 and anchor plate 122.

In a smooth-sided slot or other continuous-motion structure of the plate engagement features 114 and/or base engagement features 432, there are potentially infinite engagement stations 436, which may facilitate fine-resolution placement of the anchor plate 122 and anchoring base 102 into a desired relative rotation configuration. At least one of the plate engagement features 114 and/or base engagement features 432 could also or instead include a ratchet or detent feature configured to facilitate relative rotation of the anchor plate 122 and anchoring base 102 into one of a finite number of predefined desired relative rotation configurations in any suitable manner for a particular use environment of the present invention.

In any event, one of ordinary skill in the art can readily provide plate engagement features 114 and/or base engagement features 432 having engagement stations 436 or other structures facilitating any relative rotation between the anchoring base 102 and anchor plate 122 for a particular use environment of the present invention. This selective relative rotation between the anchoring base 102 and anchor plate 122 may be useful in operation of the apparatus 100, as described below.

Turning to FIG. 5, a partially exploded view, the apparatus 100 includes a coupler 540 and a prosthetic component 542, along with the previously described anchoring base 102, anchor plate 122, and fasteners 334. The coupler 540 is configured to couple the prosthetic component 542 with the anchor plate 122 and/or anchoring base 102 by being selectively maintained extending longitudinally through at least a portion of the central coupler aperture 124. In the embodiment shown in FIG. 5, both the anchor plate 122 and anchoring base 102 have a central coupler aperture 124a and 124b, respectively, through which at least a portion of the coupler 540 extends.

In the case of the central coupler aperture 124b of the anchoring base 102 shown in FIG. 5, at least a portion of that central coupler aperture 124b selectively accepts longitudinally therethrough at least a stem extension 544 of the coupler 540. For example, and with reference to the cross-sectional view of FIG. 2C, at least a portion of the central fastener aperture 106 is coextensive with the central coupler aperture 124b. The uppermost portion of this "dual-purpose" aperture (collectively formed by the central coupler aperture 124b and the central fastener aperture 104) has a larger diameter than the lowermost portion, for example, to provide a depth stop function for longitudinal top-down insertion of the stem extension 544.

As shown in FIG. 5, the coupler 540 includes a prosthetic-engaging portion 546. Here, the prosthetic-engaging portion 546 has an offset or eccentric relationship with the stem extension 544 and is shaped like a relatively wide and short cylinder for mating with an appropriately shaped void on an underside of the prosthetic component 542. A user presented with the apparatus 100 of FIG. 5 can therefore relatively rotate the various structures thereof (e.g., the coupler 540 and prosthetic component 542) before, during, and/or after installation of the apparatus 100 into a patient's body.

The user can secure the various structures of the apparatus into the desired relative rotational positions using any suitable attachment means (including, but not limited to, frictional engagement, adhesives, welding, fasteners, set screws, pins, attachment mechanisms, or the like) for indwelling use of the prosthetic component by the patient. For example, in the embodiment shown in FIG. 5, the stem extension 544 of the coupler 540 is selectively maintained in a position extending longitudinally through at least a portion of the central coupler aperture 124b of the anchoring base 102 via frictional engagement with that central coupler aperture 124b. It should be noted, however, that when the exploded view of FIG. 5 is assembled as described and shown herein, that at least a portion of the coupler 540 will also be extending longitudinally through the central coupler aperture 124a of the anchor plate 122, albeit without touching the structures of the anchor plate surrounding that central coupler aperture 124a.

The prosthetic component 542 shown in FIG. 5 includes at least a portion of a prosthetic articulation surface 548. As described and shown herein, the prosthetic articulation surface 548 (which articulates against another articulation surface, not shown, to form an at-least-partially prosthetic joint function) is at least a portion of a glenoid component of a reverse shoulder arthroplasty device. However, as previously noted, the prosthetic articulation surface 548 could be at least a portion of a glenoid component of a primary/standard (i.e., not reverse) shoulder arthroplasty device or could be any other prosthetic articulation surface provided for any desired use environment.

As shown in dotted line in FIG. 5, a coupler cavity 550 may be provided on the prosthetic component 542 for selective engagement (optionally, frictional engagement) with at least a portion of the coupler 540 (here, a prosthetic-engaging portion 546 of the coupler). Selective engagement between the prosthetic component 542 and at least a portion of the coupler 540 could be provided with the prosthetic articulation surface located longitudinally spaced from the anchoring base 102—for example, the anchor plate 122 could be longitudinally interposed between, and could optionally contact either or both of, the prosthetic component and the anchoring base. It is also contemplated that the prosthetic component 542 could be selectively engaged with at least a portion of the coupler 540 with the prosthetic articulation surface 548 substantially facing longitudinally away from the anchoring base 102. (Although the partially-spherical prosthetic articulation surface 548 shown in FIG. 5 could be considered to be "facing" in a number of different directions, based upon a direction normal to a local curvature, none of those "facing" directions is longitudinally toward the anchoring base 102, thus the FIG. 5 depiction is considered to have the prosthetic articulation surface 548 "substantially facing longitudinally away" from the anchoring base 102.)

FIGS. 6A-11 illustrate a second embodiment of an apparatus 100'. The apparatus 100' of FIGS. 6A-11 is similar to the apparatus 100 of FIGS. 1-5 and therefore, structures of FIGS. 6A-11 that are the same as or similar to those described with reference to FIGS. 1-5 have the same reference numbers with the addition of a "prime" mark. Description of common elements and operation similar to those in the previously described first embodiment will not be repeated with respect to the second embodiment.

In FIGS. 6A-6C, an apparatus 100' comprising an anchoring base 102' and an anchor plate 122', along with several fasteners 334', is shown in various views. FIG. 7 is a top view of an anchor plate 122', which was shown mated with the anchor plate 122' in FIGS. 6A-6C. In the detail view of FIG. 7, the anchor plate 122' is shown to have a central coupler aperture 124' which is configured to closely accept at least a portion of a coupler 540' longitudinally therethrough, in contrast with the relatively large central coupler aperture 124 of the anchor plate 122 of the first embodiment. The anchor plate 124' of the second embodiment, shown in FIG. 7, also includes an outer perimeter 126' and a plate rim 128' including a plurality of plate fastener apertures 130'. The central coupler aperture 124' of the anchor plate 122' shown in FIG. 7 is "suspended" laterally within the plate rim 128' by a plurality of crossbars or other spacing structures. The base engagement features 432' of the anchor plate 122' of FIG. 7 are shown as being through-holes, configured to engage the corresponding plate engagement features 114' of the anchoring base 102'.

Figure 8:
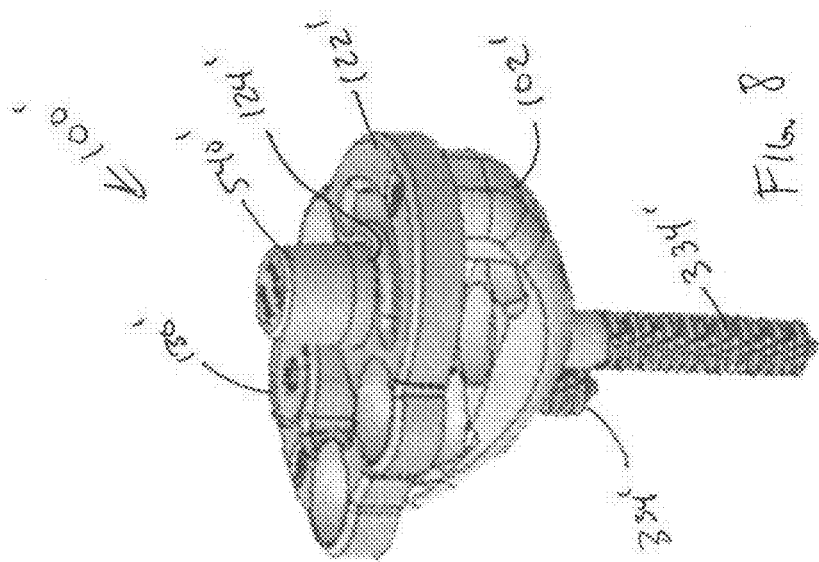
FIG. 8 is a partial perspective view of the embodiment of FIG. 6A.

FIG. 8 is an assembled partial view of the apparatus 100' of the second embodiment, with fasteners 334' passed through the central fastener aperture 106' of the anchoring base 102' and through one of the plate fastener apertures 130'. In addition, FIG. 8 depicts a coupler 540' engaged (e.g., frictionally engaged) with the central coupler aperture 124' of the anchor plate 122'.

FIG. 9 is an assembled partial view, similar to that of FIG. 8, of the apparatus 100' of the second embodiment, but with a prosthetic component 542' placed into a working position atop the anchoring base 102' and the anchor plate 122'. The coupler 540' has been received into a coupler cavity (not shown in FIG. 9) of the prosthetic component 542'. As shown in FIG. 9, a fastener aperture 952 extends from the prosthetic articulation surface 548' of the prosthetic component 542' and is in fluid communication with the coupler cavity such that a set screw or other fastener (not shown) can be passed down through the fastener aperture 952 to aid engagement between the coupler 540' and the prosthetic component 542'.

Figure 10:
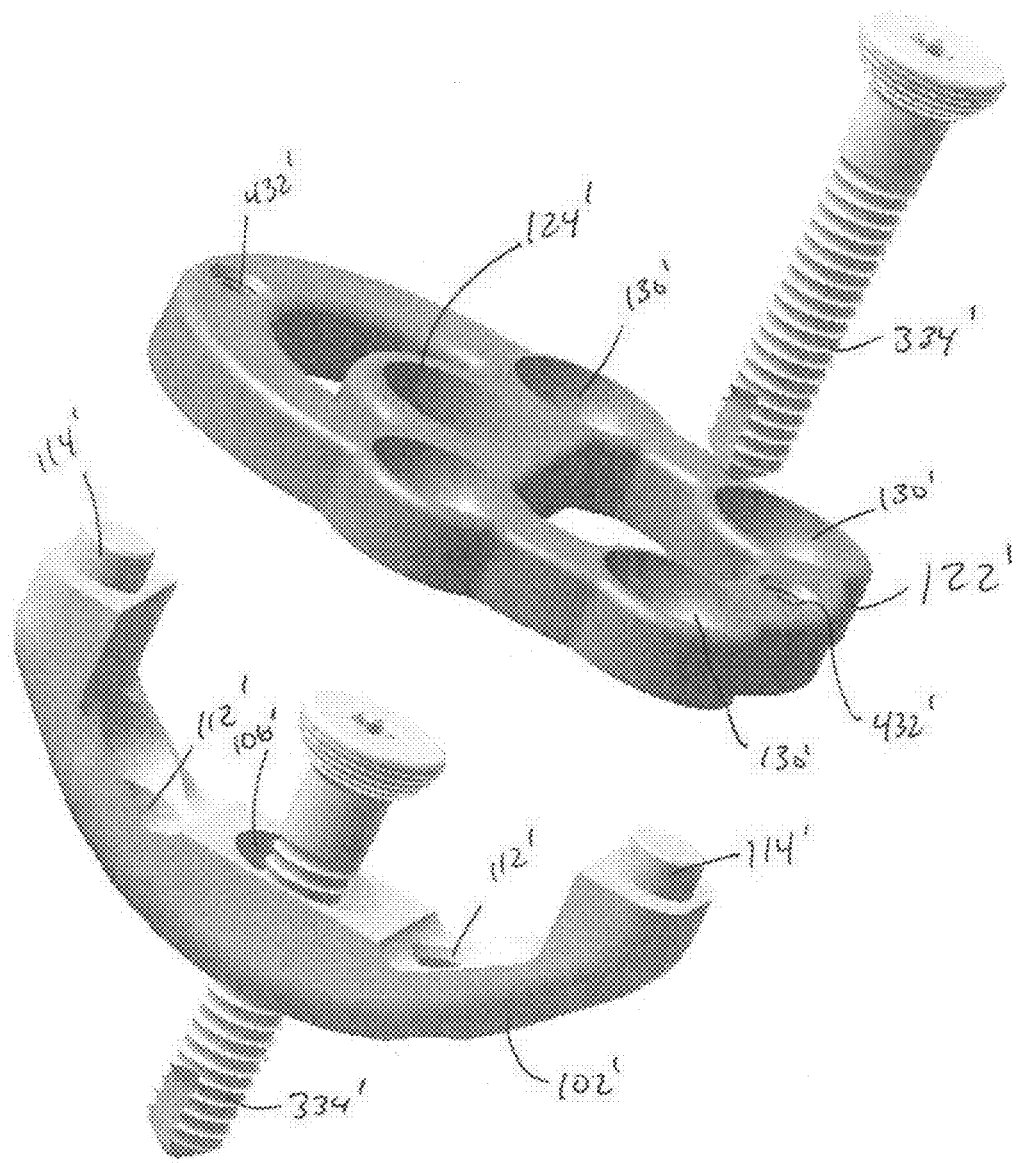
FIG. 10 is a partial exploded perspective view of the embodiment of FIG. 6A.

The exploded view of FIG. 10 shows the interrelationships among the various components of the apparatus 100' of the second embodiment.

FIG. 11 is a cross-sectional view of the apparatus 100' of the second embodiment, showing the assembled relationships of various components. It should be noted that the base engagement features 432' each include threads to facilitate usage of a set screw to help create/maintain the depicted engagement between the anchoring base 102' and the anchor plate 122'.

Several components of the second embodiment (which may be similar to corresponding components of the first embodiment) will now be specifically described in detail. FIG. 12 is a view of the anchoring base 102' component of the second embodiment, showing the central fastener aperture 106', supplemental fastener apertures 112', first and second base ends 106' and 108', first and second arms 116' and 118', and plate engagement features 114'.

FIGS. 13A-13C illustrate various example embodiments of the coupler 540', which can be used with any embodiment of the present invention. In FIG. 13A, an outward-tapering (when considered from the direction bottom-to-top of this Figure) stem extension 544' is connected to an inward-tapering (when considered from the direction bottom-to-top of this Figure) prosthetic-engaging portion 546'. The tapers of this "Morse tapered" coupler 540' may assist with frictionally engaging mated components as shown and described.

FIG. 13B shows a coupler 540' similar to that of FIG. 13A, but having a spacer 1354 of a first thickness interposed between the stem extension 544' and the prosthetic-engaging portion 546'. Similarly, FIG. 13C shows a coupler 540' similar to that of FIG. 13A, but having a spacer 1354 of a second thickness, greater than the first thickness, interposed between the stem extension 544' and the prosthetic-engaging portion 546'. The various coupler 540' designs, or any others created by one of ordinary skill in the art, may assist with providing a desired longitudinal spacing or offset between the prosthetic component 542' and at least one structure (e.g., the anchor plate 122' and/or anchoring base 102') associated with a central coupler aperture 124' which holds the coupler 540'.

FIGS. 14A-17B depict, collectively, four different combinations of sizes and coupler cavity 550' offset options for a prosthetic component 542' for use with any embodiment of the present invention. The prosthetic components 542' of FIGS. 14A-15B are of a first size, and the prosthetic components 542' of FIGS. 16A-17B are of a second size, larger than the first size. The prosthetic components 542' of FIGS. 14A-14B and 16A-16B both have coupler cavities 550' which are substantially centered on an underside thereof (as evidenced by the relatively aligned coupler cavities 550' and fastener apertures 952). The prosthetic components 542' of FIGS. 15A-15B and 17A-17B both have coupler cavities 550' which are laterally offset from "center" on an underside thereof (as evidenced by the relatively offset coupler cavities 550' and fastener apertures 952). Of course, as with all components of the present invention, one of ordinary skill in the art can provide couplers 540' and/or prosthetic components 542' for a particular use environment of the present invention.

Figure 20:
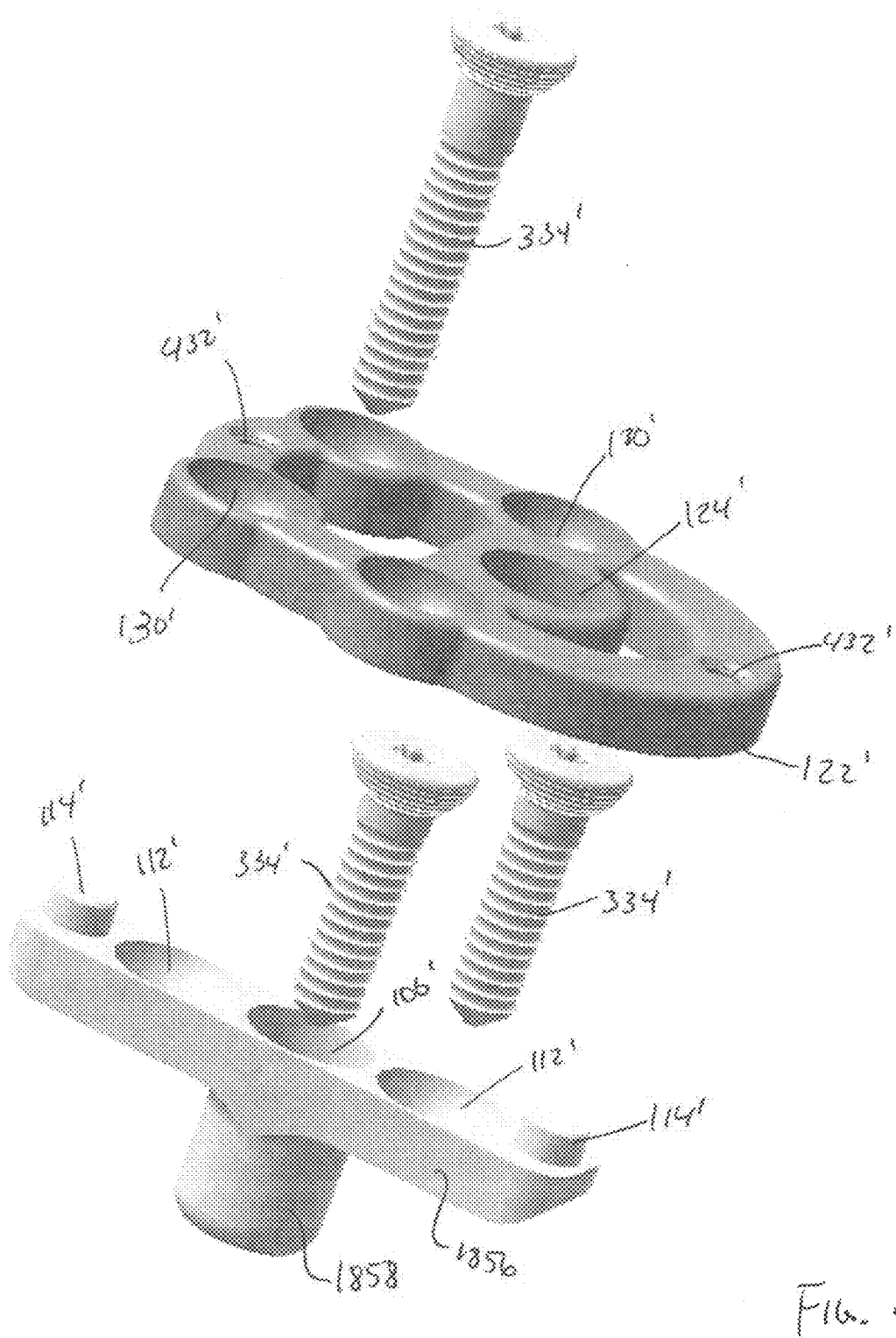
FIG. 20 is a partial exploded perspective view of the embodiment of FIGS. 19A-19B.

FIG. 18 depicts an example alternate configuration for the anchoring base 102' of the second embodiment of the present invention. In FIG. 18, the first and second base ends 108' and 110' and at least a portion of a central fastener aperture 106' are located along a laterally extending base beam 1856, with at least another portion of the central fastener aperture 106' extending through a boss 1858 projecting longitudinally downward from the base beam 1856. The plate engagement features 114' of this alternate configuration are located at opposite ends of the base beam 1856. As shown in the top and bottom perspective views of FIGS. 19A-19B, and the exploded view of FIG. 20, an anchoring base 102' having the configuration shown in FIG. 18 can be used in the second embodiment of the present invention analogously to the anchoring base 102' having the configuration shown in FIG. 12.

FIGS. 21-25B illustrate a third embodiment of an apparatus 100". The apparatus 100" of FIGS. 21-25B is similar to the apparatus 100 of FIGS. 1-5 and therefore, structures of FIGS. 21-25B that are the same as or similar to those described with reference to FIGS. 1-5 have the same reference numbers with the addition of a double "prime" mark. Description of common elements and operation similar to those in the previously described first and second embodiments will not be repeated with respect to the third embodiment.

The apparatus 100" (shown in bottom perspective view in FIG. 21 and in exploded perspective view in FIG. 22) is similar to the apparatus 199 of FIG. 5, except that the coupler 540" of the third embodiment is a two-piece construct including separate structures comprising the stem extension 544" and prosthetic-engaging portion 546". These stem extension 544" and prosthetic-engaging portion 546" structures may be connected together in any desired manner to collectively form the depicted coupler 540".

Figure 22:
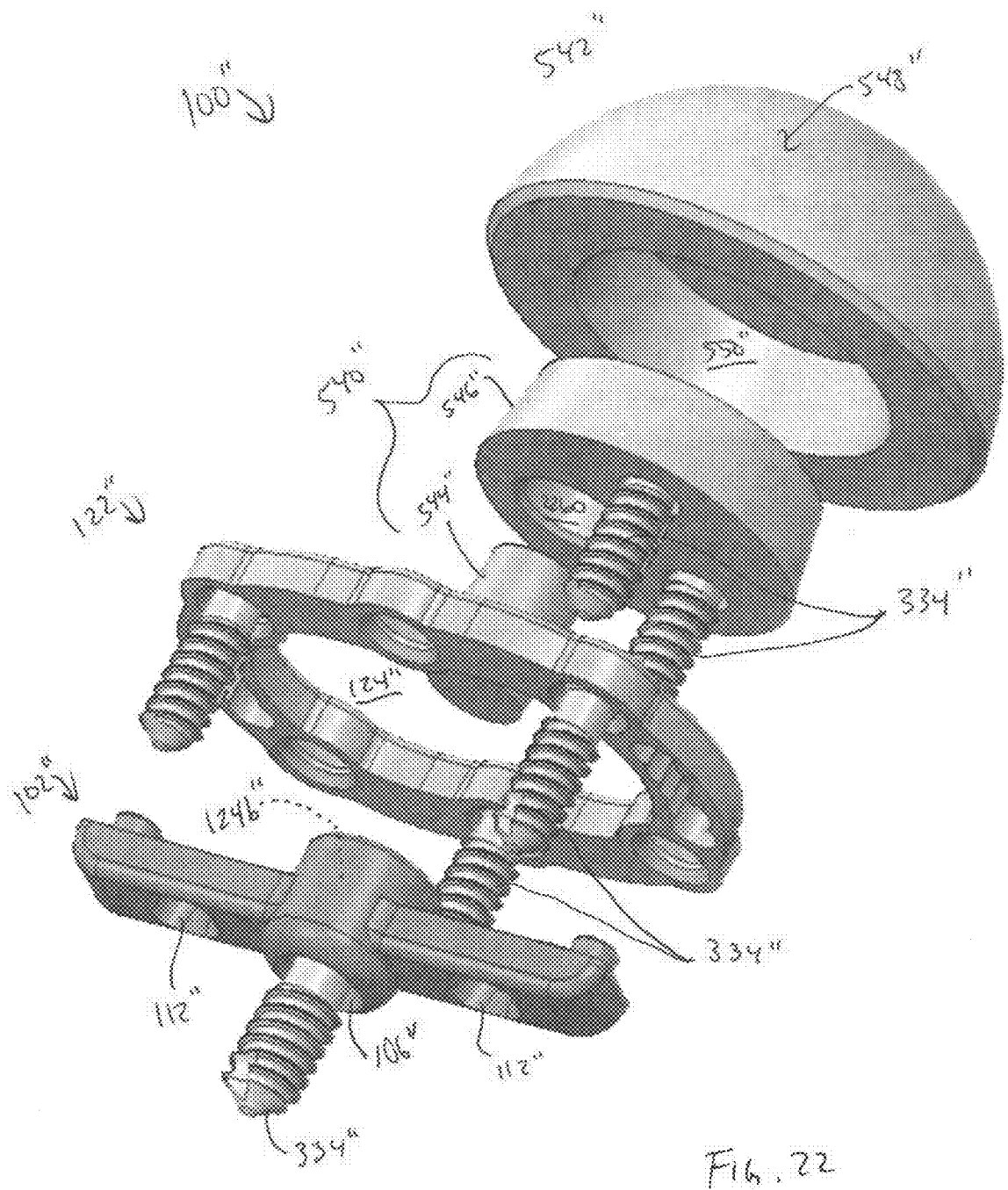
FIG. 22 is an exploded perspective view of the embodiment of FIG. 21.
Figure 23A:
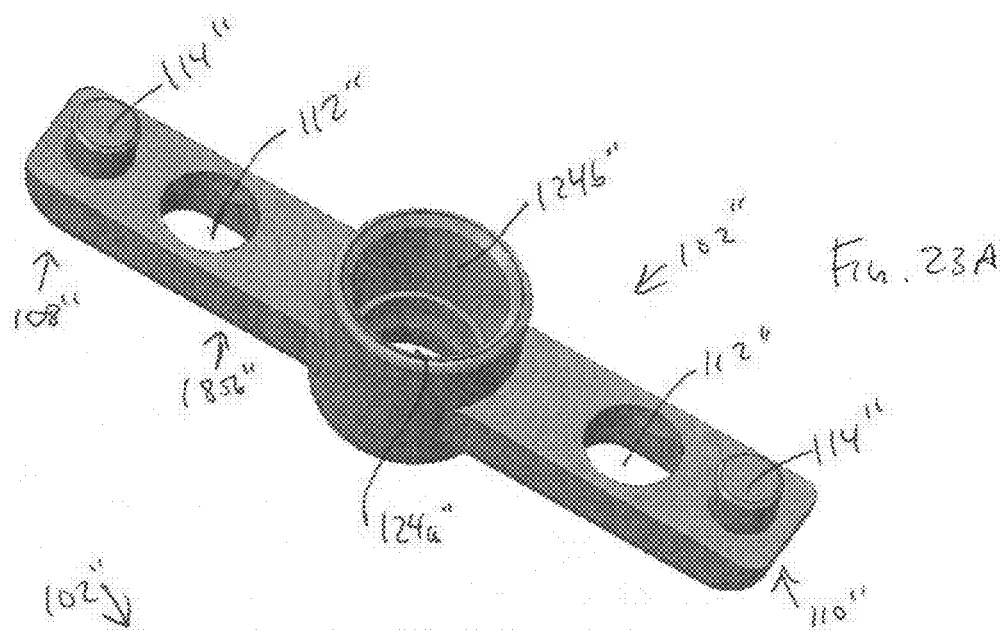
FIG. 23A is a top perspective view of a component of the embodiment of FIG. 21.
Figure 23B:
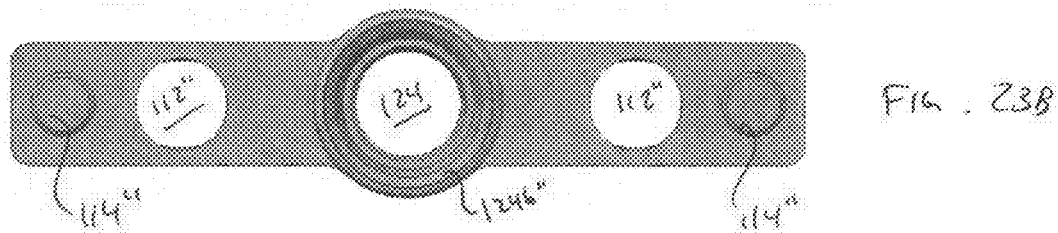
FIG. 23B is a top view of the component of FIG. 23A.
Figure 23C:
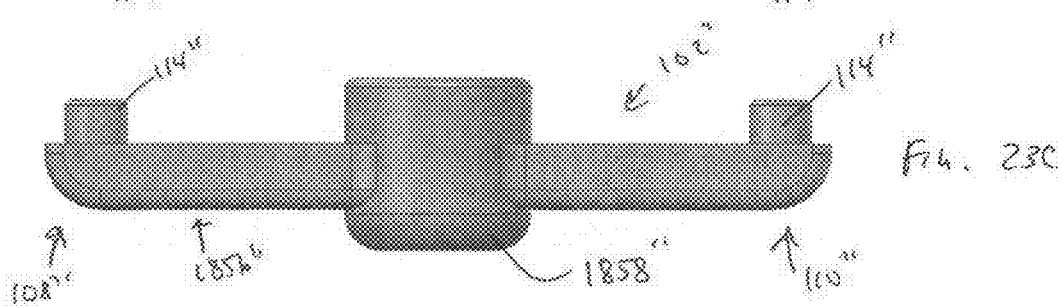
FIG. 23C is a side view of the component of FIG. 23A.
Figure 23D:
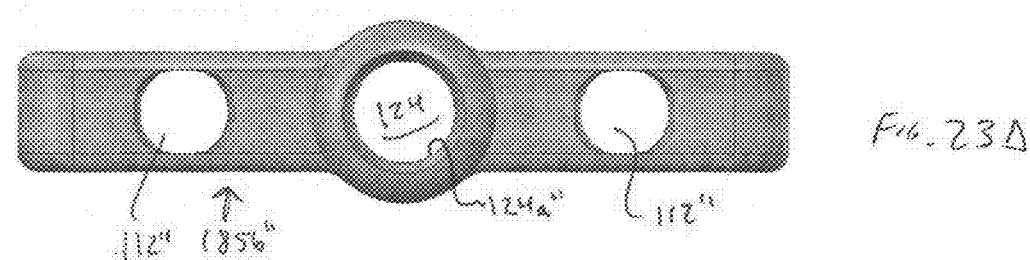
FIG. 23D is a bottom view of the component of FIG. 23A.

For example, and as shown in FIG. 22, the prosthetic-engaging portion 546" could include a stem-receiving portion 2260; here, a cavity configured to receive and hold, in any desired manner (e.g., frictional/interference fit), at least a portion of the stem extension 544" longitudinally opposite from that portion of the stem extension 544" that is selectively accepted longitudinally through at least a portion of the central coupler aperture 124b".

FIGS. 23A-23D depict various views of the anchoring base 102" of the third embodiment of the present invention, with callouts relating to the various portions of this structure similar to those of the first and second embodiments.

Figure 21:
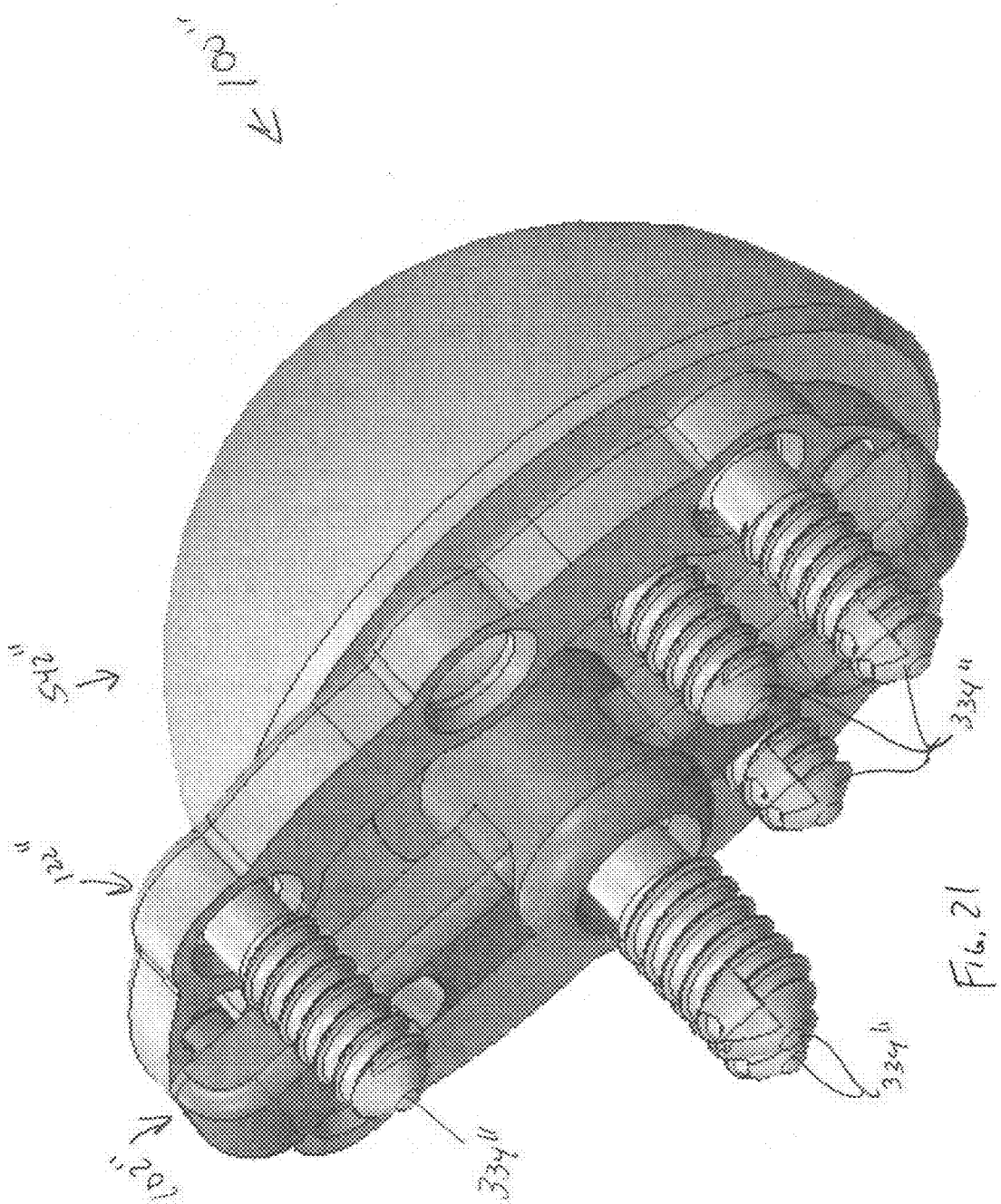
FIG. 21 is a bottom perspective view of an embodiment of the present invention.
Figure 24A:
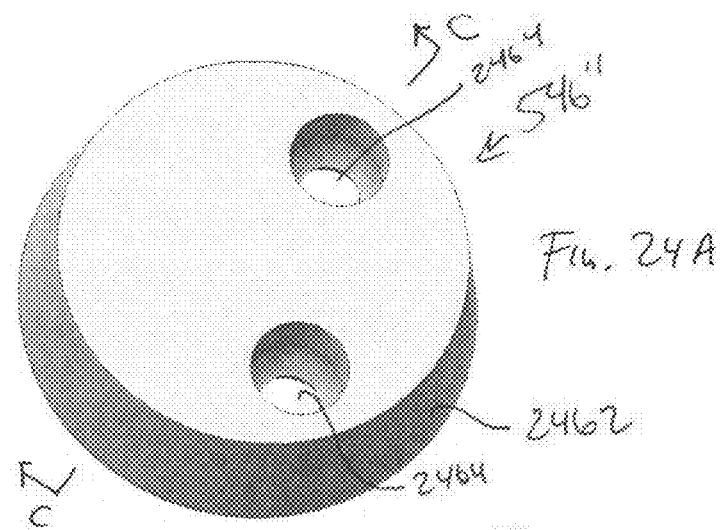
FIG. 24A is a top perspective view of a component of the embodiment of FIG. 21.
Figure 24B:
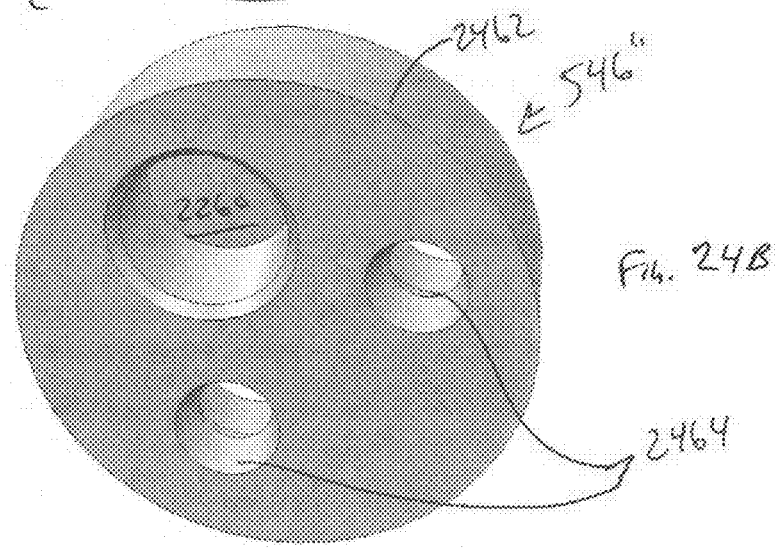
FIG. 24B is a bottom perspective view of the component of FIG. 24A.
Figure 24C:
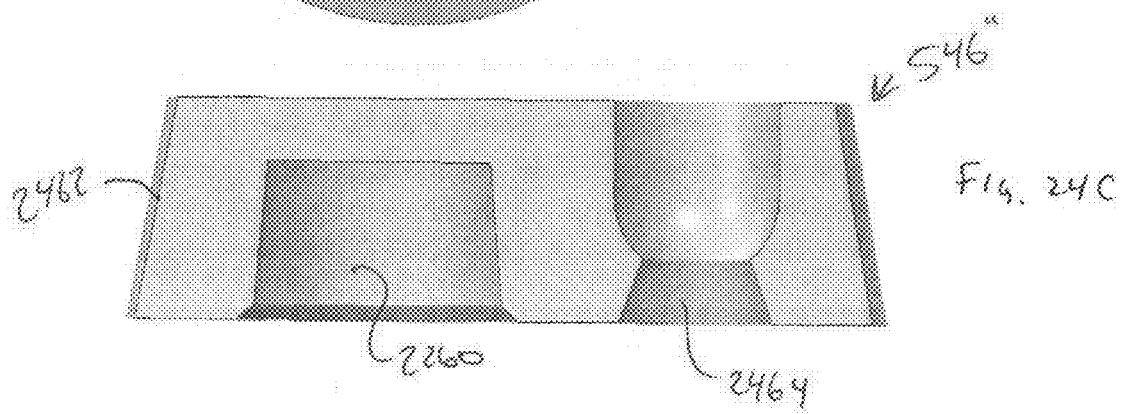
FIG. 24C is a cross-sectional view taken along line C-C of FIG. 24A.

FIGS. 24A-C depict various views of the prosthetic-engaging portion 546" of the coupler 540" of the third embodiment of the present invention, with callouts relating to the various portions of this structure similar to those of the first and second embodiments. As can be seen in these Figures, a lateral profile 2462 of the prosthetic-engaging portion 546" can be at least partially frusto-conical in shape, which may help with engaging and/or maintaining the prosthetic-engaging portion 546" with the coupler cavity 550" as shown in FIGS. 21-22.

As shown in the cross-sectional view of FIG. 24C, the stem-receiving portion 2260 is a "blind" hole (not extending through an entire thickness of the prosthetic-engaging portion 546") and also includes an at least partially frusto-conical profile, both of which may be helpful in engaging the stem extension 544" as shown and described. The prosthetic-engaging portion 546" of the coupler 540" can also include one or more coupler fastener apertures 2464, shown in FIGS. 24A-C as being through-holes, which, as with any fastener aperture described herein, are configured to accept a corresponding fastener 334" therethrough and thereby secure the prosthetic-engaging portion 546" to an underlying structure or surface, such as the anchoring base 102" and/or a patient bone surface. These coupler fastener apertures 2464 could be provided to any coupler used with the present invention. Optionally, and analogously to any fastener apertures described herein, the coupler fastener apertures 2464 could work cooperatively with a fastener 334" inserted therethrough to "sandwich" or "clamp" structures interposed between the prosthetic-engaging portion 546" and the underlying structure or surface which also receives the same fastener, and thereby prevent longitudinal (and/or lateral, depending upon fastening force) motion of such interposed structures.

Figure 25A:
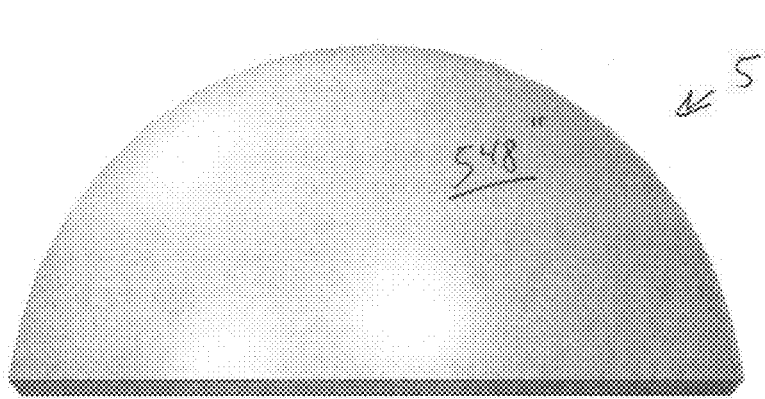
FIG. 25A is a side view of a component of the embodiment of FIG. 21.
Figure 25B:
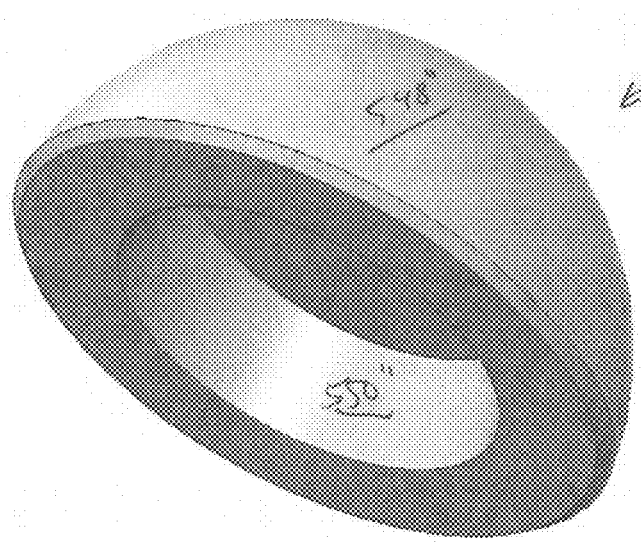
FIG. 25B is a bottom perspective view of the component of FIG. 25A.

FIGS. 25A-25B depict various views of the prosthetic component 542" of the third embodiment of the present invention, with callouts relating to the various portions of this structure similar to those of the first and second embodiments. As shown in FIG. 25B, the coupler cavity 550" of the prosthetic component 542" has an at least partially frustoconical profile, which may be configured to mate with a corresponding lateral profile 2462 of the prosthetic-engaging portion 546".

Figure 26A:
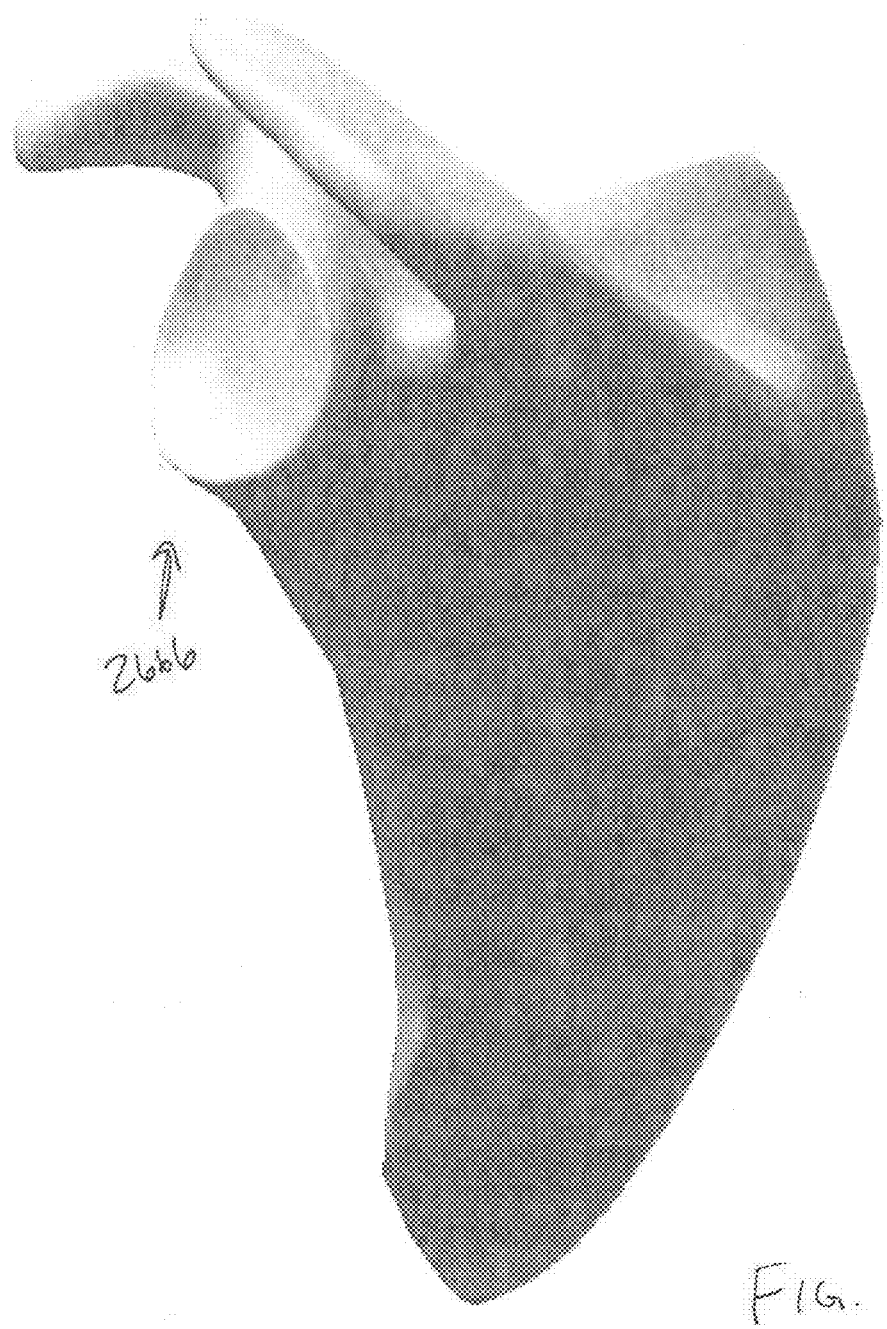
Figure 26B:
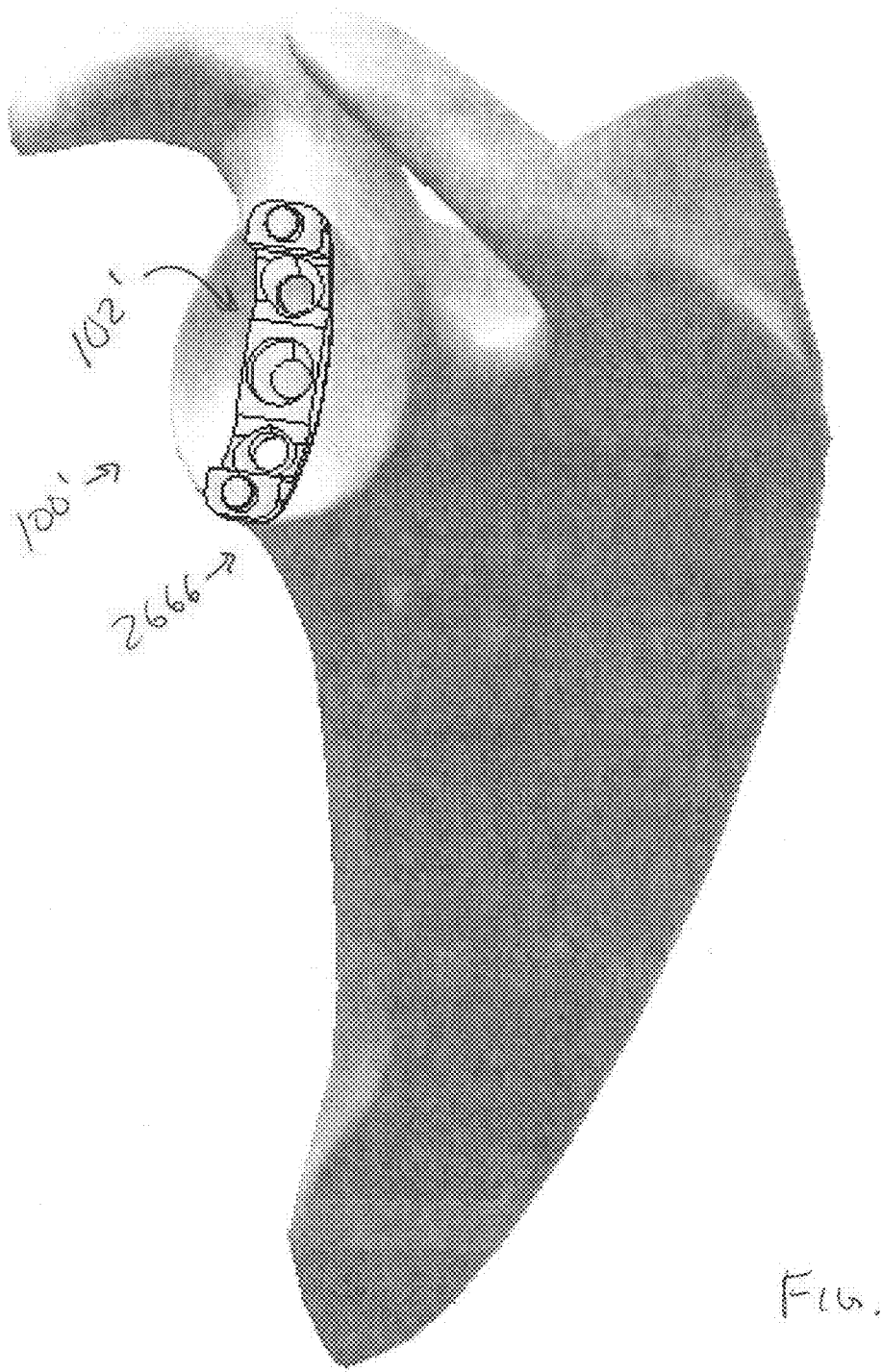
Figure 26C:
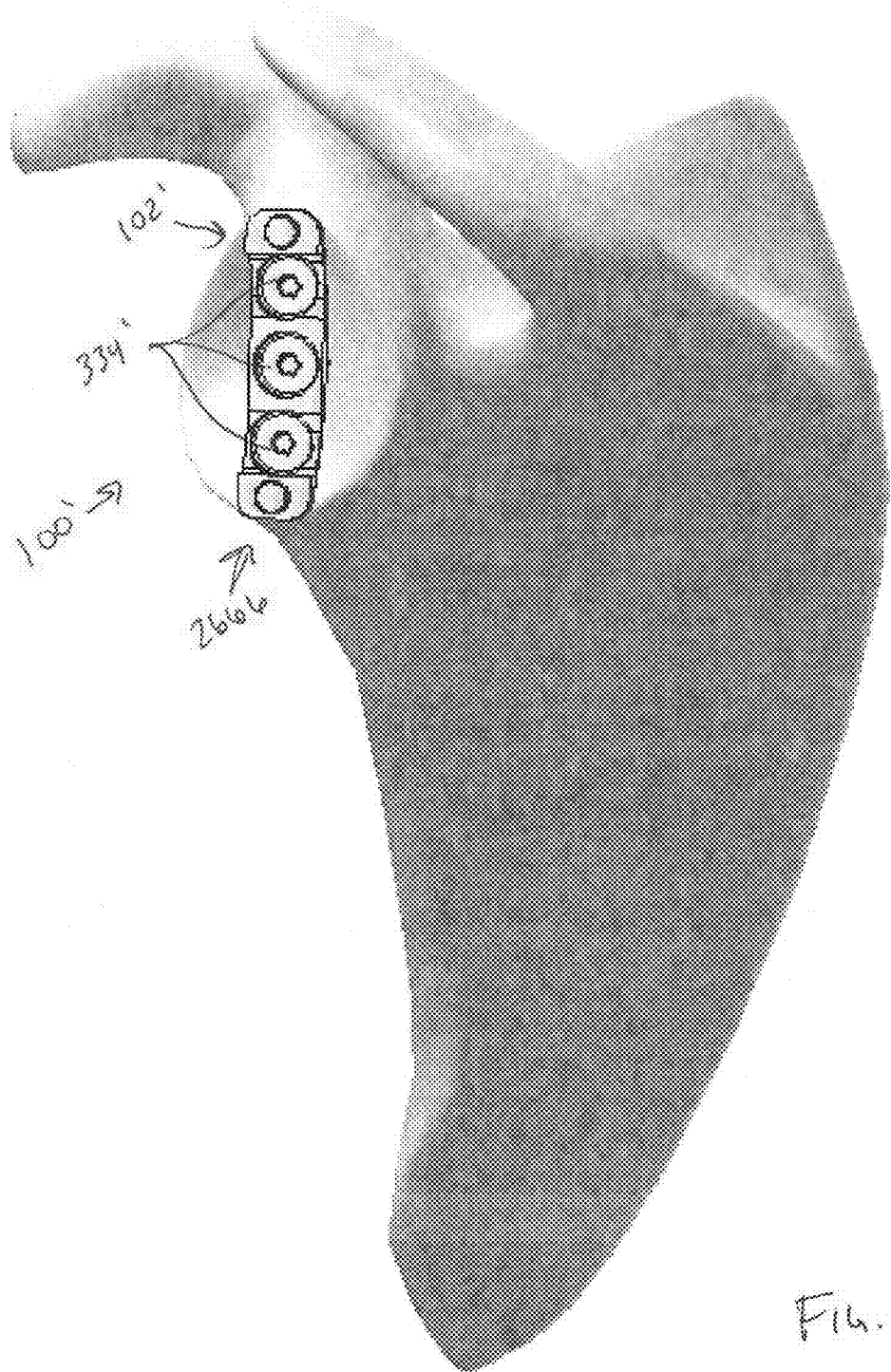
Figure 26A:
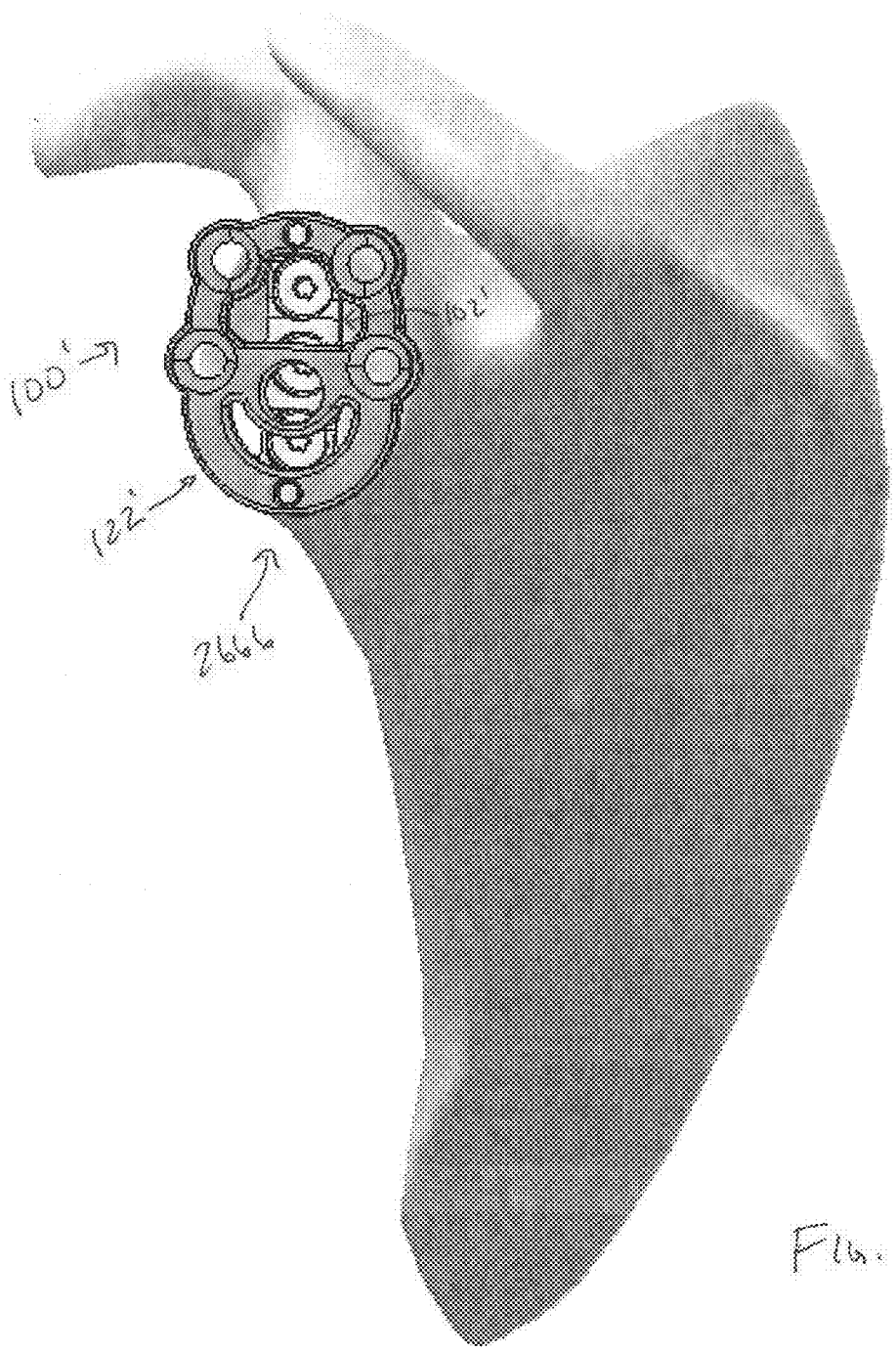

FIGS. 26A-H depict an example sequence of operation of any embodiment of the present invention, using the second embodiment (shown in FIGS. 6A-11) as an example. In FIG. 26A, a patient bone (here, shown and described as a scapula, and, more specifically, as a glenoid 2666) is provided and prepared, in any manner desired by the user, to receive the apparatus 100. FIG. 26B shows the anchoring base 102' being placed into initial contact with a surface of the glenoid 2666. In FIG. 26C, the anchoring base 102' is positioned as desired into an installation position—i.e., into a predetermined orientation with the glenoid 2666, which may differ from the orientation in which the anchoring base 102' initially contacts the glenoid. With the anchoring base 102' in the installation position, at least one fastener 334' is extended longitudinally through the central fastener aperture 106' and/or supplemental fastener apertures 112' to selectively secure the positioned anchoring base 102' to the glenoid 2666. For example, a threaded fastener could be passed through a corresponding aperture and screwed into the underlying surface/depth of the glenoid 2666. As depicted in FIG. 26C, three fasteners 334' have been used, in cooperation with the central fastener aperture 106' and two supplemental fastener apertures 112', to secure the anchoring base 102' as shown.

Figure 26E:
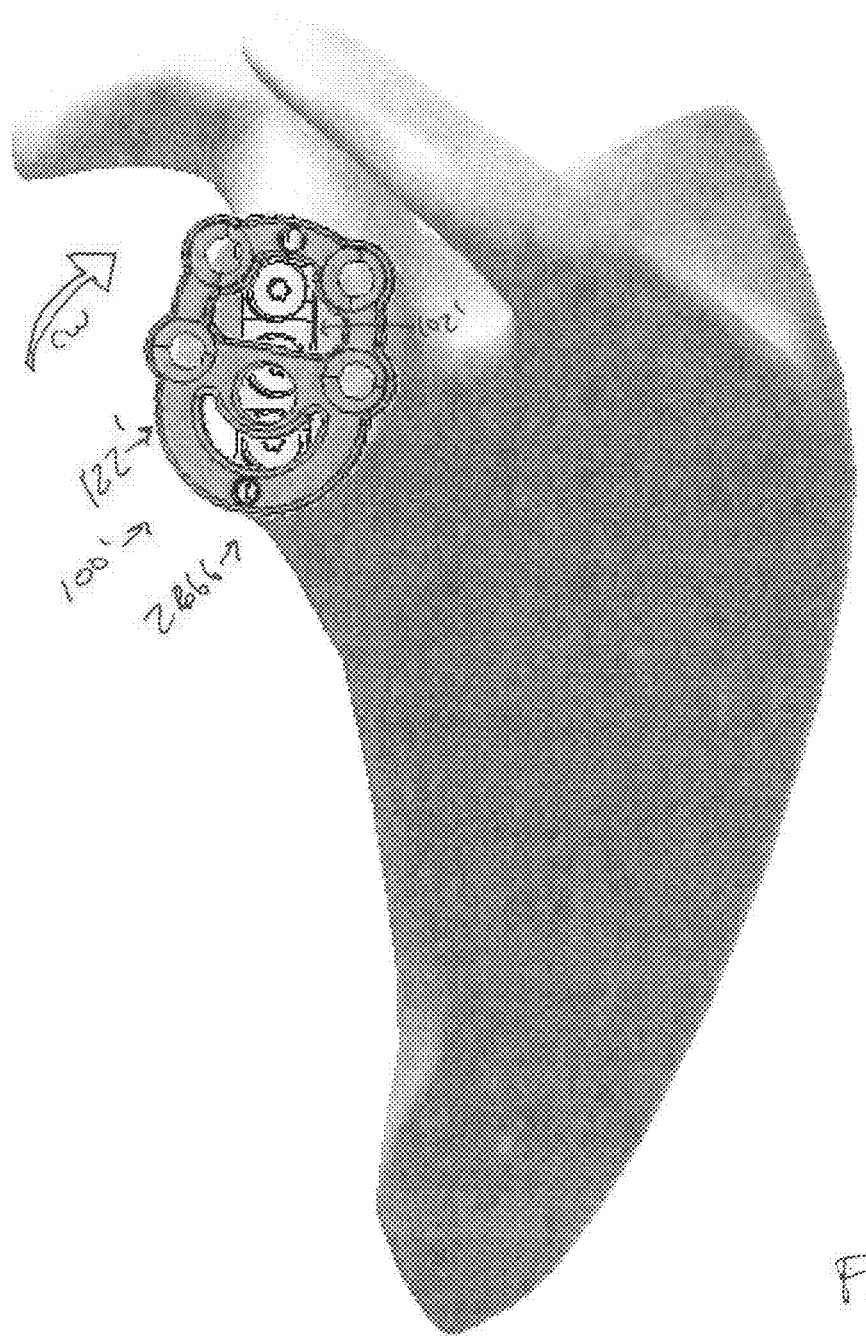

In FIG. 26D, the anchor plate 122' is brought longitudinally adjacent to, such as down onto, the anchoring base 102'. As with placement of the anchoring base 102' onto the glenoid 2666, the anchor plate 122' can be rotated and/or translated with respect to the anchoring base 102' into a desired installation position embodying a predetermined orientation, as shown in FIG. 26E by the anchor plate 122' being rotated slightly clockwise (see arrow "CW") as compared to the position of the same anchor plate in FIG. 26D. Before, during, and/or after positioning of the anchor plate 122' as desired relative to the anchoring base 102', the base engagement feature(s) 432' can be engaged with corresponding plate engagement feature(s) 114'. Any desired rotation could be facilitated by appropriately designed base engagement feature(s) 432' and/or corresponding plate engagement feature(s) 114'.

Figure 26F:
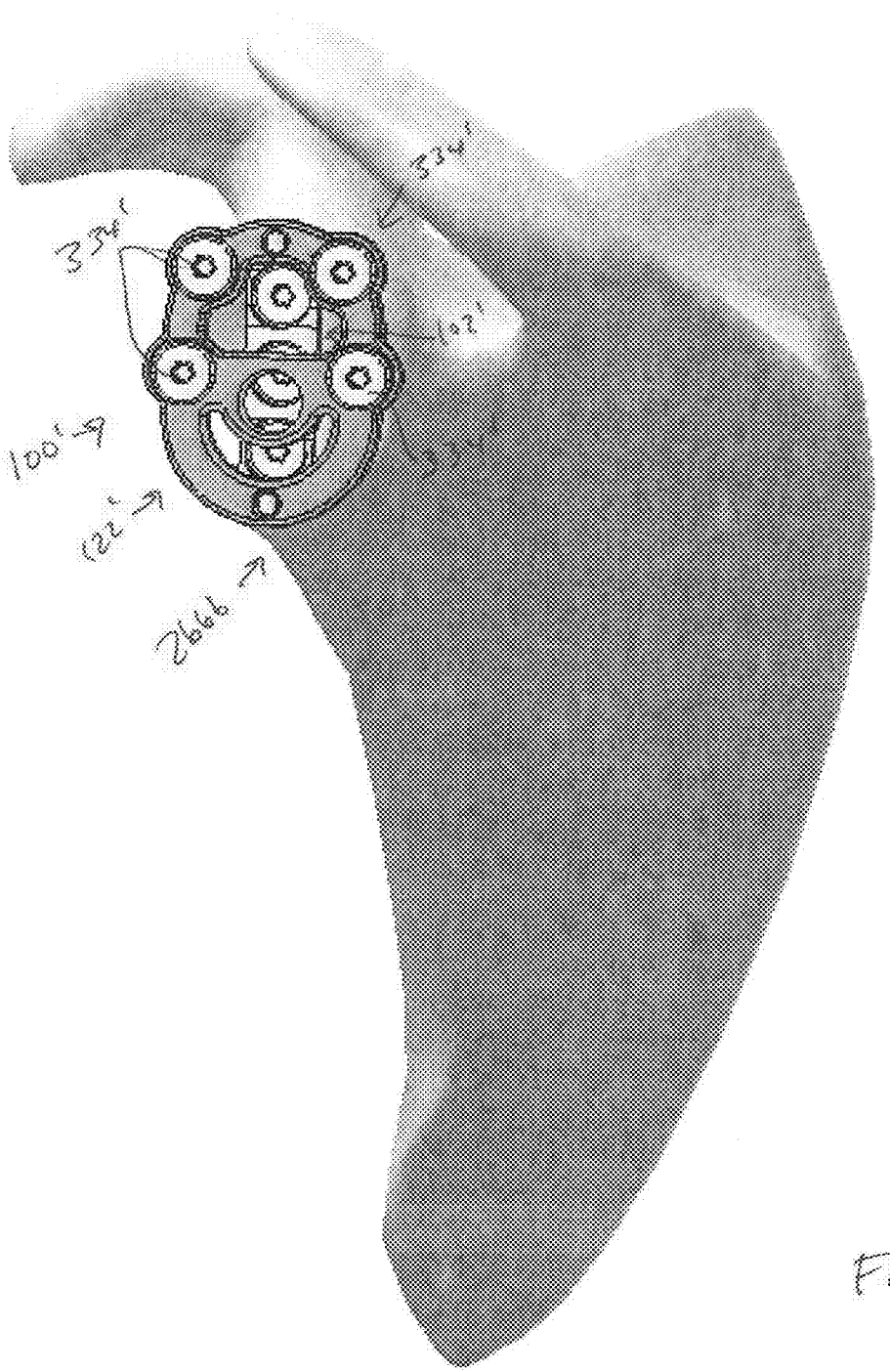

Once the anchor plate is in place as desired (here, in substantially the orientation shown in FIG. 26D), at least one fastener 334' may be extended longitudinally through at least one selected plate fastener aperture 130' to selectively secure the positioned anchoring base 102' to the glenoid 2666, as shown in FIG. 26F with four fasteners, extended through corresponding plate fasteners, as an example. For example, at least one threaded fastener could be passed through a selected plate fastener aperture 130' and screwed into the underlying surface/depth of the glenoid 2666.

Any or all of the determination of the rotational/translational relationships between the anchor plate 122' and the anchoring body 102', the selection of the fastener(s) 334', the torque applied to fastener(s) 334', any preparation steps (e.g., drilling of a pilot hole), and/or the selection of the plate fastener aperture(s) 130' to receive fasteners could be made responsive to an amount, quality, or any other property of the patient's bone. For example, if one side of the glenoid 2666 is osteoporotic and relatively fragile, the user could configure and orient the apparatus 100 (or parts thereof) to avoid mechanical contact with that deteriorated side of the glenoid 2666.

Figure 26G:
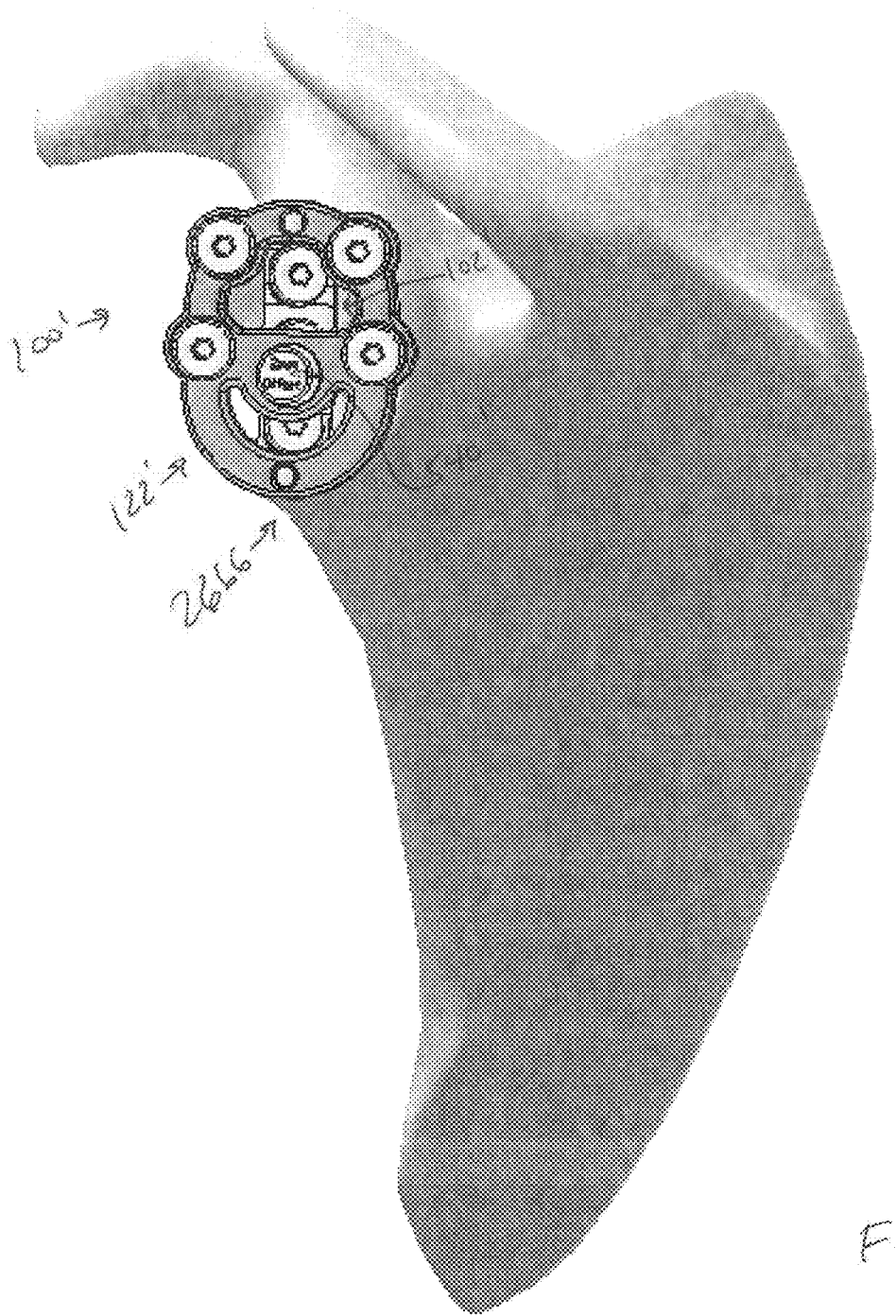

Turning to FIG. 26G, once the anchoring body 102' and anchor plate 122' are installed as desired on the glenoid, a coupler 540' can be engaged with the anchoring body 102' and/or the anchor plate 122'. For example, and as shown, the coupler 540' could frictionally engage with a central coupler aperture 124' of the anchor plate 122'.

Figure 26H:
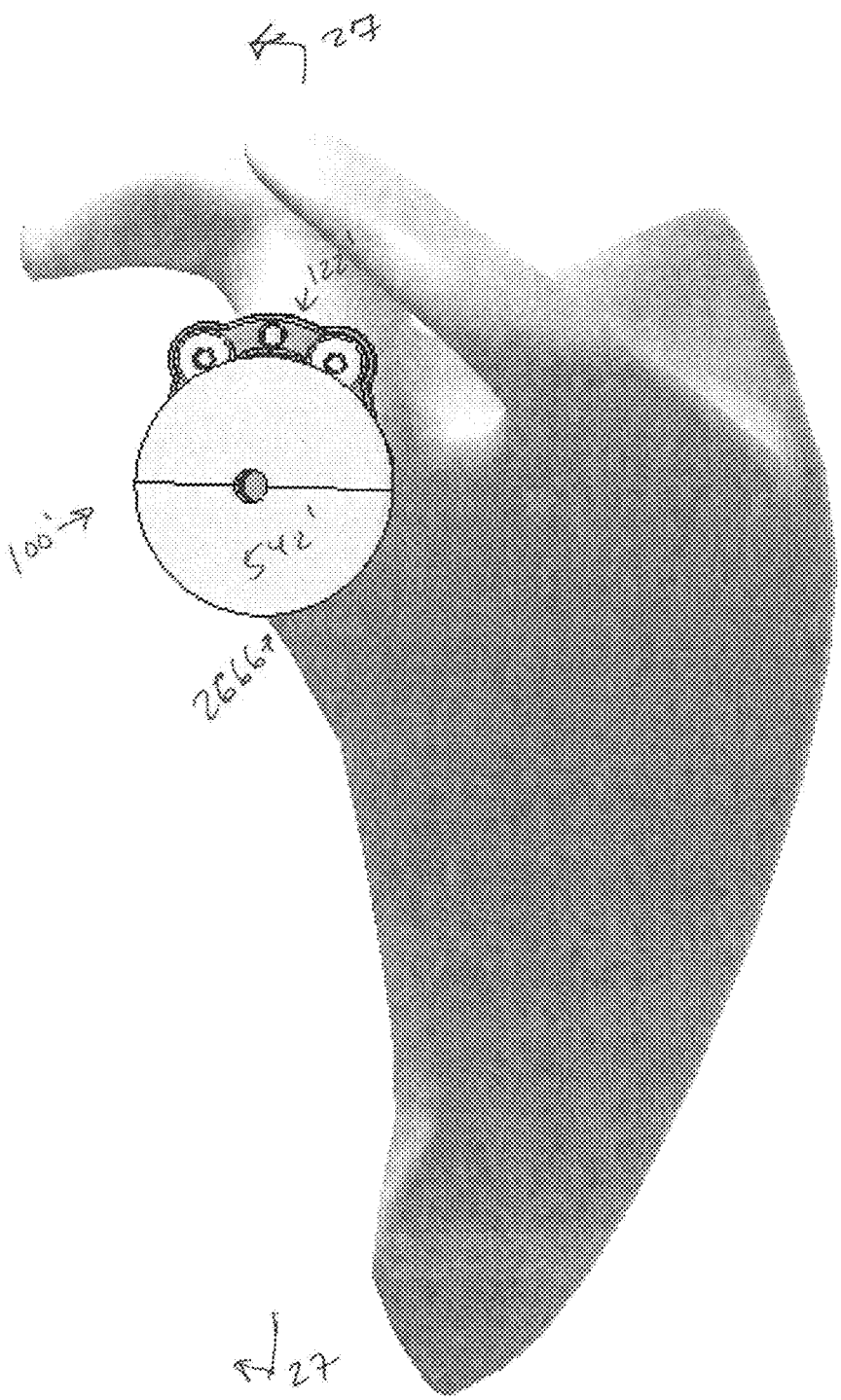

Before, during, and/or after engagement of the coupler 540' with the anchoring body 102' and/or the anchor plate 122', a prosthetic component 542' can be engaged with the coupler 540'. For example, and as shown in FIG. 26H, a coupler cavity 550' of the prosthetic component 542' could be engaged with a prosthetic-engaging portion 546' of the coupler 540'. As with all engagements shown and described herein (unless clearly described otherwise), engagement of the prosthetic component 542' with the coupler 540' could occur at least partially through frictional engagement ("press-fit") of the two structures.

Additionally or alternatively to the described frictional engagement, and as shown in FIG. 26G, a fastener could be passed through the fastener aperture 952 of the prosthetic component 542' to assist with maintenance of the components of the apparatus 100' in their "installed" or "assembled" positions.

Figure 27:
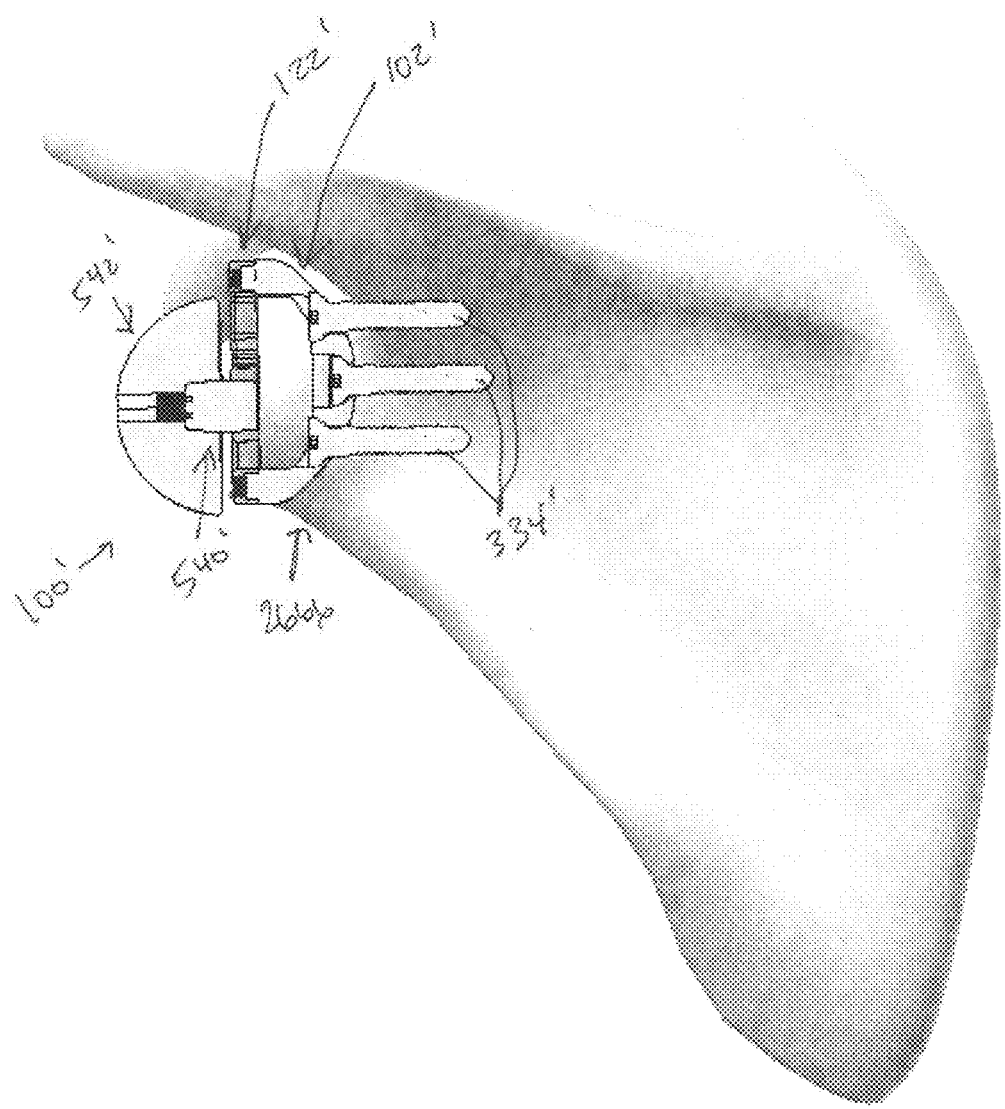
FIG. 27 is a partial cross-sectional view taken along line 27-27 of FIG. 26H.

FIG. 27 depicts a partial cross-sectional view taken along line 27-27 of FIG. 26G, showing the apparatus 100' installed into the glenoid 2666.

Should a user wish to at least partially disassemble the apparatus 100', the above steps may be reversed, in whole or part, as desired. For example, in a revision shoulder repair, the prosthetic component 542' can be removed and replaced with a second prosthetic component without removal of at least the anchor plate 122' and anchoring base 102'. It is also contemplated that all or some of the above-described sequence of actions could be reversed during surgery for any desired reason, such as to substitute a different component for an initially used, similar component—e.g., to provide a trialing feature.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the apparatus 100 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications of the present invention. While certain engagements and/or mating relationships between a plurality of structures may be described in various portions of this application as occurring using a tapered/frictional fit component, a hole-and-screw (or other fastener, and/or a set screw arrangement, it is contemplated that any suitable scheme(s) for engaging and/or fastening various structures into the relationships shown here could be used, as desired by one of ordinary skill in the art. Any elements described as "central" need not be in a geometric center of the corresponding surrounding structure—the term "central" is used in such context mainly to distinguish a "central" element from an element spaced at an extreme edge of a structure. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. It is contemplated that any number, position, and/or configuration of base engagement features 432 could be provided to an anchor plate 122 and that any number, position, and/or configuration of plate engagement features 114 could be provided to an anchoring base 102, and that, when present, the plurality of engagement stations 436 could be provided to either or both of the base and plate engagement features 432 and 114. Any component of the present invention could be provided with a user-perceptible marking to indicate a material, configuration, at least one dimension, or the like pertaining to that component, the user-perceptible marking aiding a user in selecting one component from an array of similar components for a particular use environment of the present invention. Either or both of the base and plate engagement features 432 and 114 can include one or more engagement stations 436. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. A method of facilitating the mounting of a prosthetic articulation surface to a patient tissue, the method comprising:

providing an apparatus including an anchoring base including a central fastener aperture extending longitudinally therethrough, a first base end laterally spaced from the central fastener aperture, and a second base end laterally spaced from the first base end with the central fastener aperture laterally interposed therebetween, both of the first and second base ends including a plate engagement feature, and an anchor plate including a central coupler aperture extending longitudinally therethrough, an outer perimeter spaced laterally apart from the central coupler aperture, a plate rim extending laterally inward from the outer perimeter to substantially laterally surround the central coupler aperture, at least one plate fastener aperture extending longitudinally through the plate rim, and at least one base engagement feature located on the plate rim;

placing at least a portion of the anchoring base into a predetermined orientation with the patient tissue;

extending a fastener longitudinally through the central fastener aperture to secure the anchoring base to an underlying patient tissue surface;

placing the anchor plate longitudinally adjacent to the anchoring base; and engaging at least one base engagement feature of the anchor plate with a corresponding at least one plate engagement feature of the anchoring base.

2. The method of claim 1, including extending at least one fastener longitudinally through at least one plate fastener aperture to selectively secure the anchor plate to an underlying patient tissue surface.

3. The method of claim 1, wherein providing an apparatus includes providing at least one supplemental fastener aperture extending longitudinally through the anchoring base and laterally interposed between the central fastener aperture and a chosen one of the first and second base ends, and wherein the method includes extending at least one fastener longitudinally through at least one corresponding supplemental fastener aperture to secure the anchoring base to an underlying patient tissue surface.

4. The method of claim 1, wherein engaging at least one base engagement feature of the anchor plate with a corresponding at least one plate engagement feature of the anchoring base includes engaging, in a longitudinally-oriented engagement, at least one base engagement feature of the anchor plate with a corresponding at least one plate engagement feature at least partially positioned on a topmost surface of at least one of the first and second base ends of the anchoring base.

5. The method of claim 1, wherein providing an apparatus includes providing at least one of the base engagement feature and the plate engagement features with a plurality of engagement stations and wherein engaging at least one base engagement feature of the anchor plate with a corresponding at least one plate engagement feature of the anchoring base includes selectively engaging the anchor plate with the anchoring base in a selected one of a plurality of rotational orientations within a lateral plane, responsive to a selection of engagement station used for the engagement, the plurality of rotational orientations each corresponding to a selected engagement station.

6. The method of claim 1, including selectively maintaining a coupler extending longitudinally through at least a portion of the central coupler aperture.

7. The method of claim 6, including selectively maintaining a coupler extending longitudinally through at least a portion of the central coupler aperture substantially via frictional engagement of the coupler with at least a portion of the central coupler aperture.

8. The method of claim 1, wherein providing an apparatus includes providing a prosthetic component having at least a portion of the prosthetic articulation surface located thereon, and including selectively engaging the prosthetic component with at least a portion of the coupler.

9. The method of claim 8, wherein selectively frictionally engaging the prosthetic component with at least a portion of the coupler includes selectively engaging the prosthetic component with at least a portion of the coupler with the prosthetic articulation surface longitudinally spaced from the anchoring base.

10. The method of claim 8, wherein selectively frictionally engaging the prosthetic component with at least a portion of the coupler includes selectively engaging the prosthetic component with at least a portion of the coupler with the prosthetic articulation surface substantially facing longitudinally away from the anchoring base.

* * * * *